United States Patent
Hirakawa et al.

(10) Patent No.: US 8,169,472 B2
(45) Date of Patent: May 1, 2012

(54) IMAGE DISPLAY APPARATUS WITH INTERACTIVE DATABASE

(75) Inventors: Katsumi Hirakawa, Sagamihara (JP); Seiichiro Kimoto, Hachioji (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 1116 days.

(21) Appl. No.: 12/028,919

(22) Filed: Feb. 11, 2008

(65) Prior Publication Data

US 2008/0172255 A1    Jul. 17, 2008

Related U.S. Application Data

(63) Continuation-in-part of application No. 11/577,027, filed as application No. PCT/JP2006/316339 on Aug. 21, 2006.

(30) Foreign Application Priority Data

Aug. 22, 2005  (JP) .................................. 2005-240252
Sep.  9, 2005  (JP) .................................. 2005-263090

(51) Int. Cl.
*H04N 7/18*  (2006.01)
*G06F 17/30*  (2006.01)
(52) U.S. Cl. ............................. 348/77; 348/65; 707/705
(58) Field of Classification Search .............. 348/65–77; 600/101, 109
See application file for complete search history.

(56) References Cited

U.S. PATENT DOCUMENTS

| 6,609,135 | B1 * | 8/2003 | Omori et al. ................... 358/403 |
| 6,778,223 | B2 | 8/2004 | Abe |
| 7,177,531 | B2 | 2/2007 | Horie et al. |
| 7,492,935 | B2 * | 2/2009 | Glukhovsky ..................... 348/72 |
| 7,986,337 | B2 * | 7/2011 | Davidson et al. ............... 348/77 |
| 2002/0171669 | A1 | 11/2002 | Meron et al. |
| 2003/0023150 | A1 * | 1/2003 | Yokoi et al. .................... 600/300 |
| 2003/0085994 | A1 * | 5/2003 | Fujita et al. ..................... 348/77 |
| 2004/0024616 | A1 * | 2/2004 | Spector et al. .................... 705/2 |
| 2004/0111011 | A1 | 6/2004 | Uchiyama et al. |
| 2004/0249291 | A1 | 12/2004 | Honda et al. |
| 2005/0075551 | A1 | 4/2005 | Horn et al. |

(Continued)

FOREIGN PATENT DOCUMENTS

JP     HEI10-011430     1/1998

(Continued)

OTHER PUBLICATIONS

PCT International Search Report dated Nov. 21, 2006 issued in corresponding PCT Application No. PCT/JP2006/316339.

(Continued)

*Primary Examiner* — Joshua Joo
(74) *Attorney, Agent, or Firm* — Ostrolenk Faber LLP

(57) ABSTRACT

An image display apparatus 104 according to the present invention includes a DB 130 which stores patient information of a subject, a display unit 140 that displays a group of intra-subject images of the subject and patient information, an input unit 120 that inputs at least a part of the patient information of the subject, a control unit 150, and an I/F 160 that is communicatively connected to an external receiving device. The control unit 150 searches the DB 130 for patient information of a desired subject based on information input by the input unit 120, and displays the searched patient information on the display unit 140. The patient information is transferred to the external receiving device via the I/F 160, and registered in the external receiving device.

8 Claims, 16 Drawing Sheets

U.S. PATENT DOCUMENTS

| | | | |
|---|---|---|---|
| 2005/0075555 A1* | 4/2005 | Glukhovsky et al. | 600/407 |
| 2009/0135250 A1* | 5/2009 | Davidson et al. | 348/77 |

FOREIGN PATENT DOCUMENTS

| | | |
|---|---|---|
| JP | 2001-249933 A | 9/2001 |
| JP | 2004-021767 A | 1/2004 |
| JP | 2004-041709 | 2/2004 |
| JP | 2004-321603 | 11/2004 |
| JP | 2004-337596 | 12/2004 |
| JP | 2006-061469 | 3/2006 |
| WO | WO 2005/031650 | 4/2005 |

OTHER PUBLICATIONS

Japanese Office Action mailed Feb. 9, 2010 in corresponding Japanese Patent Application No. 2005-240252 (with English language translation).

Japanese Office Action mailed Sep. 29, 2009 in corresponding Japanese Patent Application No. 2005-263090 (with partial English language translation).

Office Action issued by USPTO on Sep. 13, 2011 in connection with corresponding U.S. Appl. No. 11/577,027.

* cited by examiner

FIG.17

[NAME]   ○○○○□□□□
[Age]    △△
[Sex]    □□
[ID]     YYYY/MM/DD

CONFIRMATION

IMAGE DISPLAY APPARATUS WITH INTERACTIVE DATABASE

CROSS-REFERENCE TO RELATED APPLICATIONS

This application is a Continuation-in-Part of U.S. application Ser. No. 11/577,027, filed on Apr. 11, 2007, which is the National Stage of International Application No. PCT/JP2006/316339, filed on Aug. 21, 2006, and which claims priority from Japanese Patent Application Nos. 2005-240252, filed on Aug. 22, 2005 and 2005-263090, filed on Sep. 9, 2005, all of which are incorporated herein by reference.

BACKGROUND OF THE INVENTION

1. Field of the Invention

The present invention relates to an image display apparatus for displaying a series of images captured at multiple time points, specifically to an image display apparatus which is suitable for displaying a series of intra-subject images captured by using a capsule endoscope inserted in the subject.

2. Description of the Related Art

In recent years, a swallowable capsule endoscope has been developed in the field of an endoscope. The capsule endoscope having an imaging function and a radio communication function is inserted from a mouth into a body of a subject for an observation, and travels to capture images of the inside of organs such as the stomach, the small intestine, and the large intestine according to their peristalsis until it is naturally excreted.

While the capsule endoscope travels inside the organs, image data captured by the capsule endoscope in the subject body is sequentially transmitted to the outside of the subject by a radio signal to be stored in a memory provided in a receiving device placed outside of the subject, or displayed on a display provided to the receiving device. A doctor, a nurse, or the like can make a diagnosis based on images displayed on a display of an image display apparatus based on the image data stored in the memory, or images displayed on the display provided to the receiving device simultaneously with the data reception by the receiving device (see Japanese Patent Application Laid-Open No. 2003-19111).

The receiving device as described above performs an initialization before receiving image data from the capsule endoscope by acquiring patient information which identifies an examined subject from an image display apparatus which displays a group of intra-subject images, deleting patient information acquired at a previous examination, and newly registering the newly acquired patient information. In addition, the receiving device is configured to check whether a subject to whom the receiving device is attached is a target subject or not at a time of attachment before receiving image data from the capsule endoscope.

Patient information registered in the receiving device can identify a subject by including plural types of information (such as patient name, date of birth, date of examination, and ID information) of a subject to whose body interior the capsule endoscope is inserted. In the conventional image display apparatus described above, however, when the patient information of the subject is to be registered in the receiving device, all types of information included in the registered patient information have to be input one by one for each examination. Thus the registration of the patient information in the receiving device is cumbersome.

In view of the above, an object of the present invention is to provide an image display apparatus which can easily search for desired patient information of a subject from a database in which patient information of plural subjects is stored, displays found patient information, and reduce a labor for inputting patient information at a time of registration of the patient information to the receiving device of a group of intra-subject images.

SUMMARY OF THE INVENTION

To solve the problems as described above and to achieve an object, an image display apparatus according to one aspect of the present invention includes a database that stores patient information including plural pieces of information of a subject, a display unit that displays a group of intra-subject images of the subject captured by a capsule endoscope and patient information, an input unit that inputs at least a part of information included in patient information of a desired subject, a control unit that searches the patient information of plural subjects stored in the database for the patient information of the desired subject based on the at least a part of information input by the input unit, to display the searched patient information on the display unit, and a communication unit that transmits the patient information searched by the control unit to an external receiving device that receives a group of intra-subject images from the capsule endoscope in the desired subject.

Further, in the image display apparatus according to another aspect of the present invention, the database may store case data which includes at least patient information of a subject and a group of intra-subject images, the input unit may input at least a part of information of related information of the desired subject, and the control unit may search case data of plural subjects stored in the database for case data including the at least a part of information input by the input unit to display the searched case data on the display unit.

Further, in the image display apparatus according to still another aspect of the present invention, the related information may be one of patient information and diagnosis data of a subject.

Further, in the image display apparatus according to still another aspect of the present invention, the control unit may search for plural pieces of patient information including the at least a part of information input by the input unit, to display a list of searched plural pieces of patient information on the display unit.

Further, in the image display apparatus according to still another aspect of the present invention, the control unit may search for plural pieces of case data including the at least a part of information input by the input unit, to display a list of searched plural pieces of case data on the display unit.

Further, in the image display apparatus according to still another aspect of the present invention, the communication unit may be selectively connected to one of an external server having a database storing patient information of plural subjects and an external receiving device for communication, and the control unit may select one of the database of the external server connected to the communication unit for communication and the database, search the patient information of plural subjects stored in the database selected for patient information including the at least a part of information input by the input unit, and display the searched patient information on the display unit.

Further, in the image display apparatus according to still another aspect of the present invention, the communication unit may be selectively connected to one of an external server having a database storing case data of plural subjects and an external receiving device for communication, the control unit may select one of the database of the external server connected to the communication unit for communication and the database, search the case data of plural subjects stored in the database selected for case data including the at least a part of information input by the input unit, to display the searched case data on the display unit.

Further, in the image display apparatus according to still another aspect of the present invention, the input unit may input confirmation completion information indicating that the patient information searched by the control unit is confirmed, and the control unit may determine that confirmation of the patient information is completed based on the confirmation completion information, and control the communication unit to transmit the patient information whose confirmation is completed to the external receiving device.

Further, in the image display apparatus according to still another aspect of the present invention, the input unit may input confirmation completion information indicating that the patient information searched by the control unit is confirmed, and the control unit may determine that confirmation of the patient information is completed based on the confirmation completion information, and displays the case data including the patient information whose confirmation is completed on the display unit.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 17 is a diagram illustrating one example of patient information displayed on a display unit of the display apparatus.

DETAILED DESCRIPTION OF THE PREFERRED EMBODIMENTS

Exemplary embodiments of a radio system for acquiring intra-subject information as a preferred embodiment of an image display apparatus according to the present invention will be explained in detail with reference to the accompanying drawings. However, the present invention shall not be limited to the embodiments. Throughout the drawings, the same part is denoted by the same numeral.

First Embodiment

Figure 1:
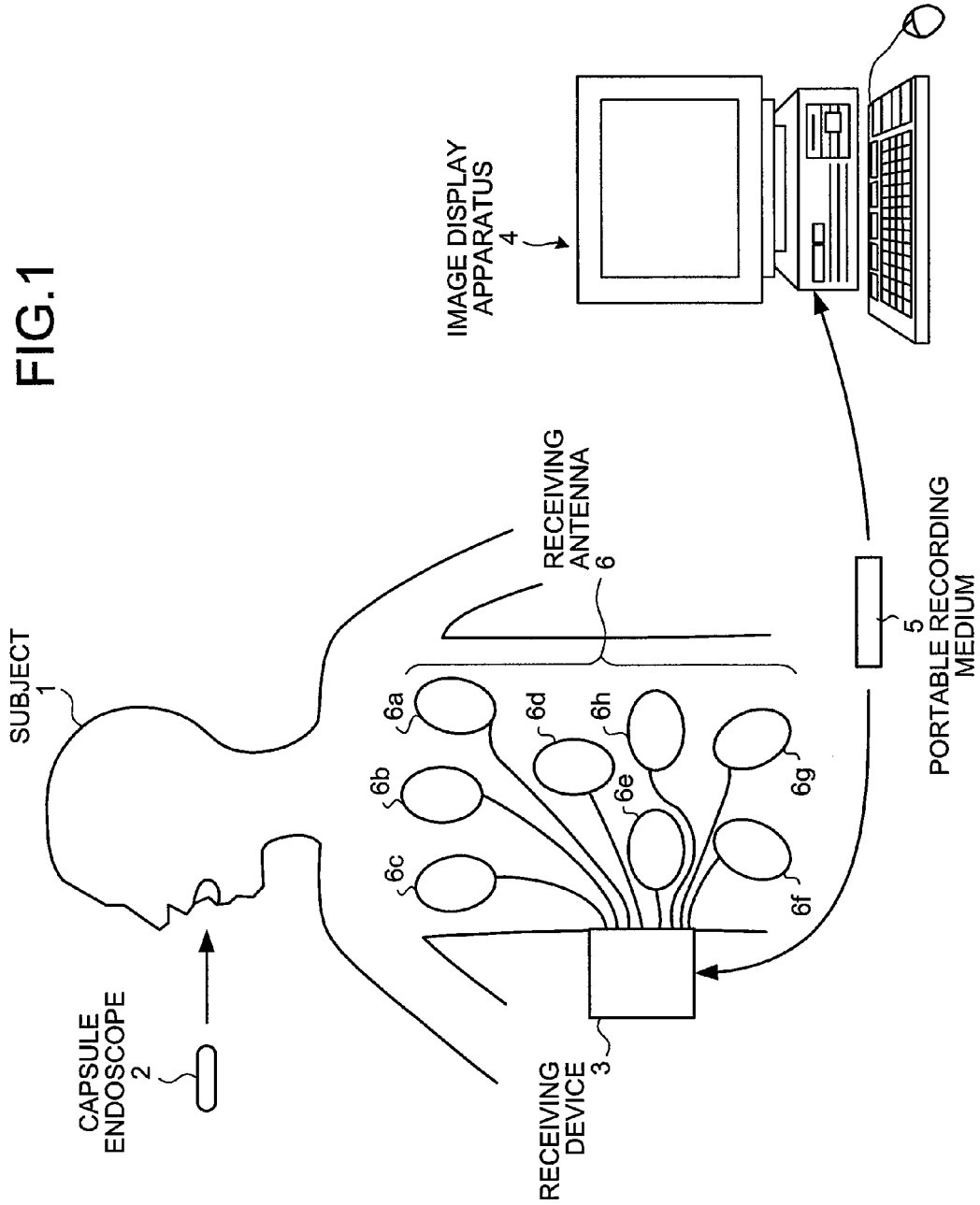
FIG. 1 is a schematic diagram of a configuration of a radio system for acquiring intra-subject information according to a first embodiment.

First, a radio system for acquiring intra-subject information provided with an image display apparatus according to a first embodiment will be explained. FIG. 1 is a schematic diagram of an entire configuration of the radio system for acquiring intra-subject information. The radio system for acquiring intra-subject information uses a capsule endoscope as one example of a body-insertable device.

As shown in FIG. 1, the radio system for acquiring intra-subject information includes a capsule endoscope 2 which is inserted into a body of a subject 1 to wirelessly transmit image data of a captured intra-subject image to a receiving device 3; the receiving device 3 which receives the image data wirelessly transmitted from the capsule endoscope 2; an image display apparatus 4 which displays the intra-subject image based on an image signal received by the receiving device 3; and a portable recording medium 5 which transfers image data and the like between the receiving device 3 and the image display apparatus 4.

The receiving device 3 include a receiving antenna 6 having a plurality of antennas 6a to 6h which are attached on an outside surface of the subject 1. The receiving device 3 receives image data and the like wirelessly transmitted from the capsule endoscope 2 via the receiving antenna 6, and records every piece of the received image data so as to associate with reception intensity information of respective antennas 6a to 6h at the time of data reception.

The antennas 6a to 6h realized by a loop antenna for example, are disposed at predetermined positions on the outside surface of the subject 1, i.e., positions respectively corresponding to organs as a path of the capsule endoscope 2 inside the subject 1. The antennas 6a to 6h may be arranged at predetermined positions on a jacket or the like to be worn by the subject 1. In this case, the antennas 6a to 6h are arranged at predetermined positions on the outside surface of the subject 1 through the jacket or the like. An arrangement of the antennas 6a to 6h may be changed arbitrarily depending on the purposes such as an observation, a diagnosis, or the like of the subject 1. The number of antennas provided to the receiving antenna 6 is not necessarily limited to eight as explained here as antennas 6a to 6h, and may be less or more than eight.

The image display apparatus 4 realized by a work station having a cathode-ray tube (CRT), a liquid crystal display, or the like for example, displays an image based on image data obtained via the portable recording medium 5 or the like. The image display apparatus 4 may output the image data to an output device such as a printer. The image display apparatus 4 has a function of communicating with an external device, and obtains/outputs the image data via wired or radio communication.

The portable recording medium 5 realized by a compact flash (registered trademark) memory, CD, DVD and the like, is detachable with respect to the receiving device 3 and the image display apparatus 4, and can record or output various types of information such as the image data and the like when the portable recording medium 5 is attached to the receiving device 3 and the image display apparatus 4. For example, the portable recording medium 5 is attached to the receiving device 3 and records the image data and the like transmitted from the capsule endoscope 2 to the receiving device 3, while the capsule endoscope 2 travels inside the subject 1. After the capsule endoscope 2 is discharged from the subject 1, the portable recording medium 5 is removed from the receiving device 3 and attached to the image display apparatus 4 to output the recorded image data and the like to the image display apparatus 4. Since the image data is transferred between the receiving device 3 and the image display device 4 via the portable recording medium 5, the subject 1 can freely move while the capsule endoscope 2 is in the subject 1. The image data may be transferred through wired or radio communication between the receiving device 3 and the image display apparatus 4.

Figure 2:
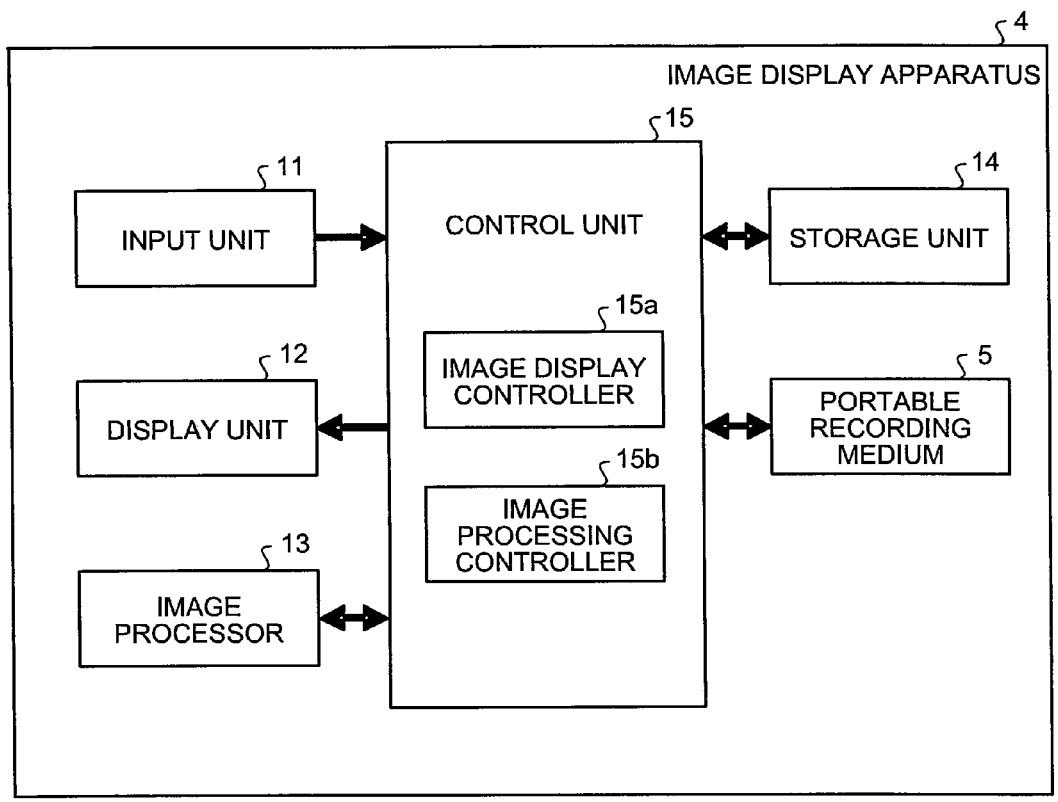
FIG. 2 is a block diagram of a configuration of an image display apparatus according to the first embodiment.

Next, a configuration of the image display apparatus 4 according to the first embodiment will be explained. FIG. 2 is a block diagram of a configuration of the image display apparatus 4. As shown in FIG. 2, the image display apparatus 4 includes an input unit 11 which allows inputting various types of information; a display unit 12 which displays the various types of information; an image processor 13 which processes the input image; a storage unit 14 which stores the various types of information; and a control unit 15 which controls the processing and operation of each unit of the image display apparatus 4. The input unit 11, the display unit 12, the image processor 13, and the storage unit 14 each are electrically connected to the control unit 15. The image display apparatus 4 further includes an interface for the portable recording medium 5 so that the portable recording medium 5 can be detachably equipped. The portable recording medium 5 is electrically connected to the control unit 15 when attached to the image display apparatus 4.

The input unit 11 includes various switches, an input key, a mouse, a touch screen, and the like, and inputs various types of information such as selection-information of an image to be displayed. An observer of the displayed image as an operator of the image display apparatus 4 performs various operations of reading the displayed image, image selection, image recording and the like via the input unit 11. The input unit 11 may include an interface for wired or wireless communication such as a universal serial bus (USB), IEEE1394, or the like so that images can be input by an external device.

The display unit 12 includes a liquid crystal display and the like, and displays various types of information such as image data. Particularly, the display unit 12 displays various data such as image data stored in the portable recording medium 5 or the storage unit 14, and the Graphical User Interface (GUI) window which requests the observer or the like of the image display apparatus 4 to input various types of processing information.

The storage unit 14 is realized by a ROM in which various processing programs and the like are stored in advance, and a RAM which stores processing parameters for each processing, processing data, and the like. The storage unit 14 can store image data input via the portable recording medium 5 and the like, image data processed by the image processor 13, display control data processed by an image display controller 15a, and the like.

The image processor 13 obtains image data from the portable recording medium 5 or the storage unit 14 based on a control by an image processing controller 15b, and performs various image processing on the obtained image data, such as a concentration conversion (gamma conversion and the like), a smoothing (noise elimination and the like), a sharpening (edge emphasis and the like), an image recognition (detection of featured-image area, computing of an average color, and the like), and the like.

The control unit 15 is realized by a central processing unit (CPU) and the like which execute various processing programs stored in the storage unit 14. Specifically, the control unit 15 includes the image display controller 15a and the image processing controller 15b. The image display controller 15a controls to display a series of images captured at multiple time points as image data stored in the portable recording medium 5 or the storage unit 14 on the display unit 12. As the series of images specifically in the first embodiment, a series of images which capture the inside of organs of the subject 1 at multiple time points are displayed.

Specifically, the image display controller 15a controls to display a time scale indicating an imaging period of the series of the intra-subject images, and to display an operation icon as an appending unit that appends marker information indicating that a main display image displayed in a predetermined main display area among the series of the intra-subject images is an image of interest. The operation icon is, for example, displayed as an operation button on the GUI screen.

Based on the imaging time point of the image of interest to which the marker information is appended, the image display controller 15a further controls to display on the time scale a display area which represents a time before an imaging time point of the image of interest or a time after the imaging time point of the image of interest, so as to be discriminable from other display areas on the time scale. Here, a determination of which to display either the display area before the imaging time point or the display area after the imaging time point depends on the type of the marker information appended to the image of interest. When there are multiple images of interest to which the marker information is appended, the image display controller 15a controls to display a display area between imaging time points of respective images of interest so as to be discriminable from other display areas on the time scale.

For realizing the discriminative display, the image display controller 15a controls to display at least one of hue, color saturation, luminance, design (pattern), shape, and size of a desired display area on the time scale so as to be discriminable from the other display areas. Here, the desired display area to be discriminated from the other display areas on the time scale is one of two areas which are divided by an imaging time point of an image of interest on the time scale. Specifically, the image display controller 15a controls to discriminably display the display area before the imaging time point of the image of interest and the display area after the imaging time point of the image of interest by differentiating at least one of hue, color saturation, luminance, design (pattern), shape, and size on the time scale.

The image display controller 15a controls to display an image of interest to which the marker information is appended, as a thumbnail in a display sub-area separately from the main display area, and further controls to display a relative time corresponding to an imaging time point of each thumbnail near the displayed thumbnails each. In this case, the image display controller 15a can control to display relative times of respective thumbnails based on an imaging time point of a reference thumbnail which is arbitrarily selected from thumbnails displayed in the display sub-area.

The image display controller 15a controls to display an operation icon and the like as a selection-information acquiring unit that acquires selection-information for selecting the reference thumbnail. The operation icon is, for example, displayed as an operation button for exclusive use on the GUI screen, or an invisible operation button overlapped with the thumbnail. A clicking operation on the operation icon by using a mouse provided to the input unit 11, for example, executes inputting predetermined selection-information. The information display controller 15a can also control to update the reference whenever selection-information is acquired according to the execution of clicking on the operation icon and the like, i.e., whenever selection-information is updated, and to display a relative time based on an updated reference imaging time point.

The image processing controller 15b obtains image data stored in the portable recording medium 5 or the storage unit 14 to output to the image processor 13, and controls various image processing of the output image. The image processing controller 15b outputs the image data which is the result of processing in the image processor 13 to the storage unit 14 or the portable recording medium 5 for storage.

Figure 3:
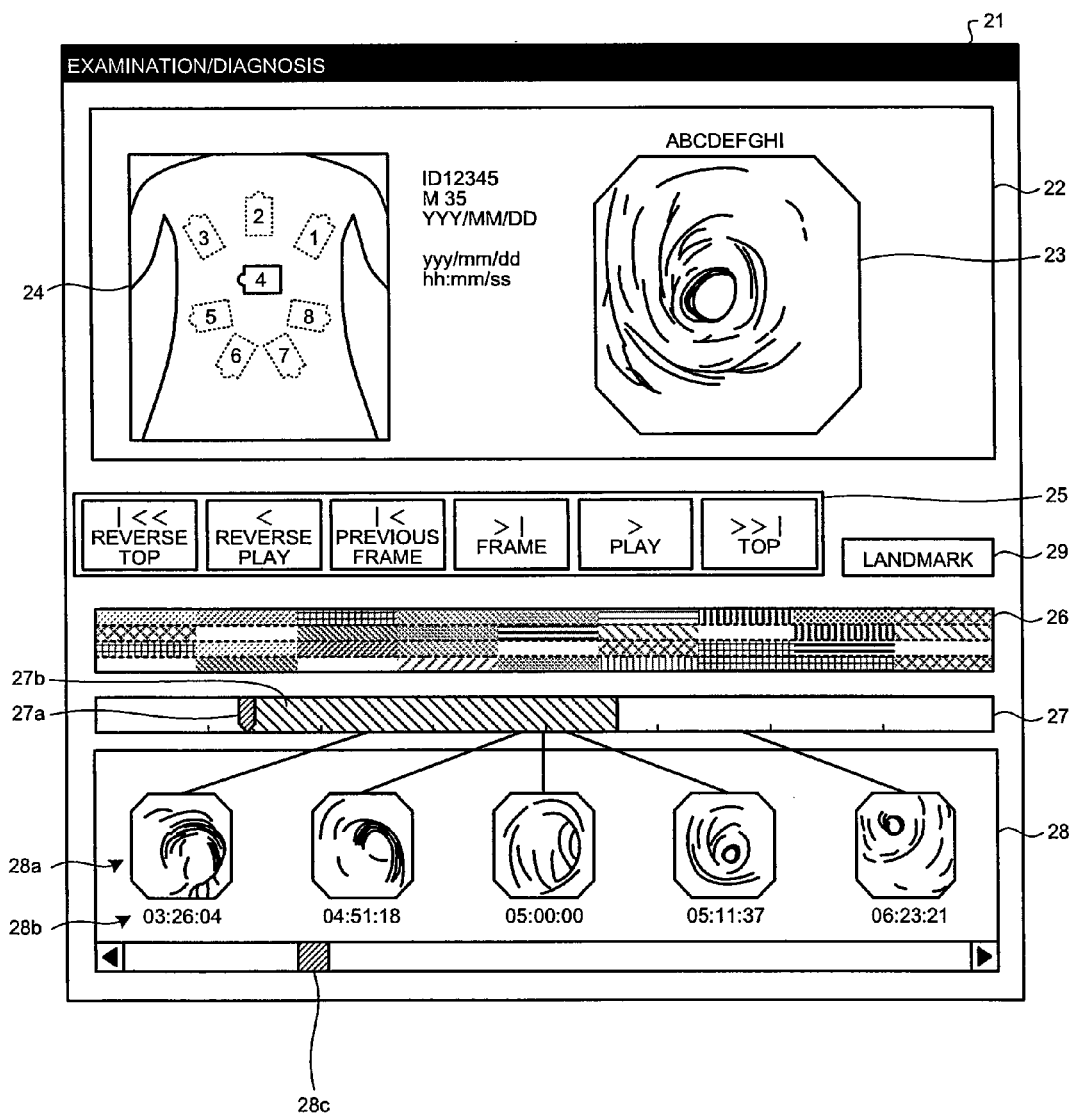
FIG. 3 is a diagram illustrating a display screen image of the image display apparatus shown in FIG. 1.

Next, the display screen (GUI screen) which is displayed on the display unit 12 in the image display apparatus 4 will be explained. FIG. 3 is a diagram illustrating one example of the GUI screen displayed based on a control by the image display controller 15a in the image display apparatus 4. As shown in FIG. 3, the display unit 12 displays a window 21 ("Examination/Diagnosis" window) as the GUI screen. The window 21 includes a main display area 22 which displays a main display image and the like; an image operation area 25 which has various image operation buttons shown as an icon; a color bar 26 and a time bar 27 as a time scale indicating an imaging period of the series of intra-subject images; and a display sub-area 28 which exhibits a thumbnail and the like, each being arranged from top to bottom in parallel according to the order described above.

The main display area 22 exhibits a main display image 23 which is an image selected from the series of intra-subject images based on instruction information input by the input unit 11; and an antenna arrangement plan 24 which schematically illustrates an arrangement of the antennas 6a to 6h on the outside surface of the subject 1. The main display area 22 further includes textual information of name, ID number, sex, age, birth date, imaging date, imaging time, and the like of the subject 1, which are associated with the intra-subject image selected as the main display image 23. The main display area 22 can house predetermined two or more number of main display images according to a predetermined operation.

The antenna arrangement plan 24 schematically illustrates an arrangement of the antennas 6a to 6h together with a partial contour of the subject 1. In the antenna arrangement plan 24, an antenna number as an identification of each antenna is shown near each of the antennas 6a to 6h. In FIG. 3, numerals "1" to "8" are denoted for the antenna number, for example. In the antenna arrangement plan 24, the antenna which has maximum reception intensity among the antennas 6a to 6h when the intra-subject image displayed as the main display image 23 is captured, is exhibited discriminably from the other antennas. FIG. 3 is a diagram illustrating a state where, as an antenna having maximum reception intensity, the antenna denoted by "4" is shown discriminably from the other antennas, for example. To realize a discriminative display, the image display controller 15a can control to display at least one of luminance, hue, and color saturation, of the antenna having the maximum reception intensity so as to be discriminable from the other antennas.

In the color bar 26, average colors of images in the series of intra-subject images are exhibited respectively in the time-series order as a whole. Specifically, a display area of each imaging time point on the color bar 26 indicates an average color of each intra-subject image captured at each imaging time point. Since the series of intra-subject images have organ-specific average colors respectively, the observer or the like can recognize the organ captured in the intra-subject image of each imaging time point based on the transition of the average colors along the time axis (lateral axis in FIG. 3) on the color bar 26.

The color bar 26 has a format where the entire display area thereof is divided into four in the lateral direction on the display screen. Divided color bars of respective divided levels indicate time-series average area-colors or time-series average period-area colors on respective levels, which respectively correspond to divided image areas of the series of intra-subject images. In other words, the average colors of respective intra-subject images are computed per each divided image area of the entire image area divided into four, and average area-colors or average period-area colors of respective divided image areas are displayed on the color bar 26 in an order corresponding to the divided order, for each of four divided scale areas which are separated as a result of division in the lateral direction of the display area of each time point.

According to the color bar 26, the observer or the like not only can recognize organs captured in intra-subject images at multiple time points, respectively based on the transition in the average colors along the time axis of the divided color bar of each divided level, but also can easily estimate the detailed condition inside the captured organ depending on the divided image areas. Accordingly, when an average color of a red color group is visually recognized on a divided color bar 26a which is the top level of four levels for a certain period, for example, the observer or the like can recognize that a bleeding portion is present inside the organ whose image is captured in the period, the bleeding portion is present within the imaged range corresponding to the divided image areas on the top level of all intra-subject images in the period, and the like. Moreover, when an average color of a black color group in an image area including the luminal portion is displayed on a level of the divided color bars different from the level on which an average color of the other image areas is displayed, the observer or the like can recognize the condition of the inside of organs within the imaged range excluding a luminal portion.

A slider 27a which is movable in the time axis direction is displayed on the time bar 27. The slider 27a indicates an imaging time point of an intra-subject image displayed as a main display image 23 on the time bar 27, and moves on the time bar 27 in response to a changeover of the main display image 23. For example, when any one of image operation buttons in the image operation area 25 is operated via a mouse and the like (not shown), an image displayed as the main display image 23 is changed from one to another, and then the slider 27a moves to a position indicating the imaging time point of the intra-subject image displayed as the main display image 23 after the changeover.

In contrast, when the slider 27a is operated to move by the mouse and the like, an intra-subject image corresponding to an imaging time point which is indicated by the moved slider 27a is displayed as the main display image 23. When the slider 27a is operated to move in a row, images are each changed and displayed as the main display image 23 in a row correspondingly to the operations. According to the slider 27a, the observer or the like can operate to move the slider 27a to an imaging time point corresponding to an intra-subject image of a desired organ which is picked out with reference to the color bar 26, so that the intra-subject image can be displayed immediately as the main display image 23.

Further, a marker 27b for indicating an imaging period of a group of images each recognized as an image of interest among the series of intra-subject images is displayed discriminably from the other display areas on the time bar 27. In FIG. 3, for example, the marker 27b is displayed in a color different from the color for the other display areas, so that the observer or the like can visually and easily recognize the imaging period of the group of images of interest.

A start time point (time point at the left end of the marker 27b) and an end time point (time point at the right end of the marker 27b) of the imaging period indicated by the marker 27a are set by an operation of a landmark button 29 serving as an operation icon for appending marker information to an intra-subject image. Specifically, an intra-subject image at an imaging time point which is set to the start time point of the marker 27b is displayed as the main display image 23. Then, the intra subject image as the main display image 23 is appended with marker information indicating the start time point by executing a clicking operation or the like on the landmark button 29 via the mouse (not shown). In the same manner, an intra-subject image at an imaging time point which is set to the end time point of the marker 27b is displayed as the main display image 23, and marker information indicating the end time point is appended to the image displayed as the main display image 23. When the start time point and end time point are set in such a manner, the marker 27b is displayed to clearly indicate the designated imaging period.

According to the marker 27b, the observer or the like can easily recognize that the intra-subject images within the imaging period designated by the marker 27b are the images of interest which should specially be paid attention to. Since information of the marker 27b, i.e., marker information indicating the start and end time points of the marker 27b is recorded so as to be associated with intra-subject images, the imaging period in which an image of interest is present can be displayed whenever the series of intra-subject images are displayed. Accordingly, it is possible to reduce the time and effort the observer or the like requires for image search, and to perform an observation of images of interest effectively.

The left ends of the color bar 26 and the time bar 27 as serving as a time scale, indicate an imaging time point of the first image of the time-series intra-subject images. The right ends thereof indicate an imaging time point of the last image of the time-series intra-subject images. Normally, the imaging time point at the left end corresponds to a start time point of image data reception by the receiving device 3, and the imaging time point at the right end corresponds to an end time point of the image data reception.

In the display sub-area 28, an image selected and extracted from the series of intra-subject images is displayed as a thumbnail 28a. Specifically, the intra-subject image displayed as the main display image 23 according to a predetermined button operation or mouse operation is additionally displayed in the display sub-area 28 as the thumbnail 28a.

In the display sub-area 28, each thumbnail has individual additional information displayed in the neighborhood as textual information 28b. As the textual information 28b, an imaging time of each of the displayed thumbnails, a relative time which corresponds to each of the imaging time points based on a predetermined reference time point, and comments appended by the observer or the like are shown. In FIG. 3, for example, relative times corresponding to respective imaging time points of thumbnails based on the reference imaging time point of the first image of the time-series images are shown as the textual information 28b.

Figure 4:
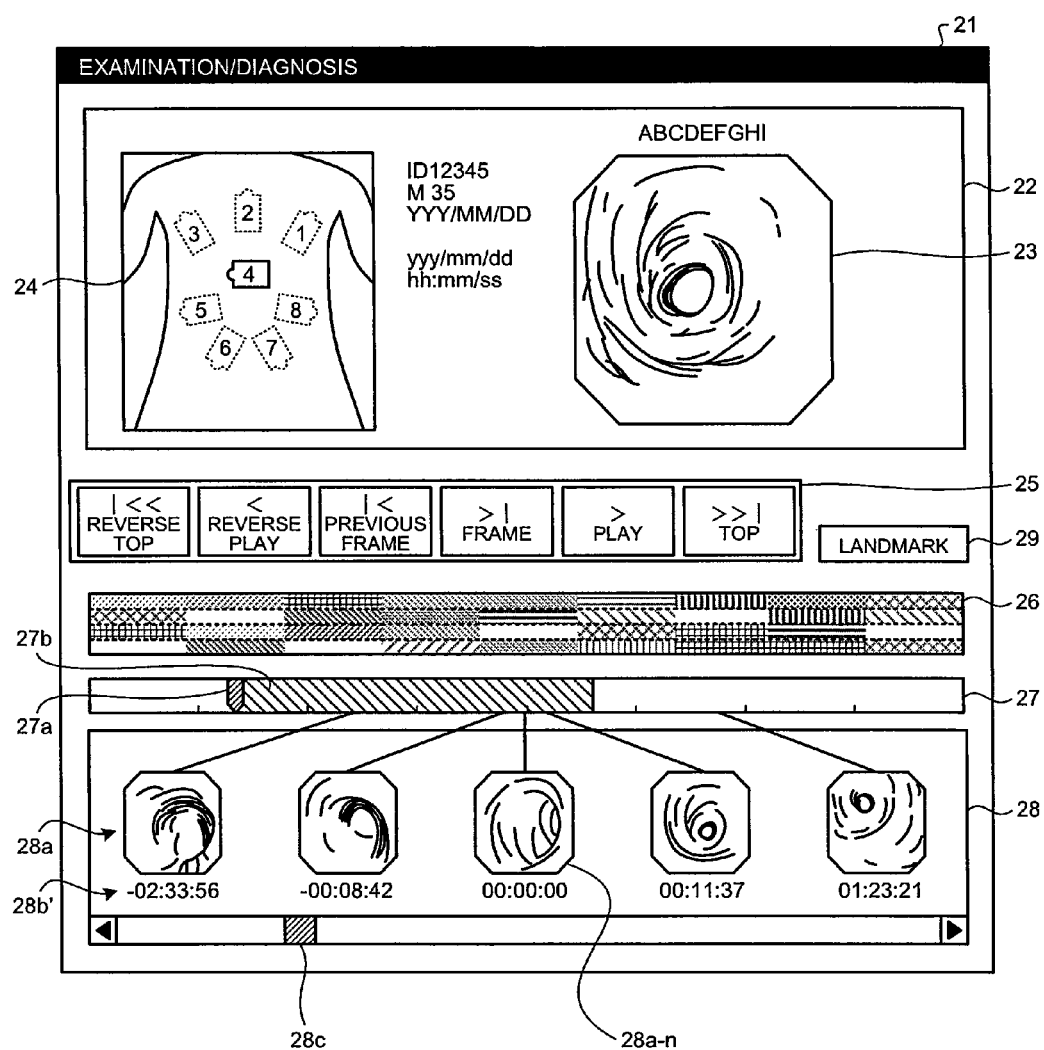
FIG. 4 is a diagram illustrating another display screen image of the image display apparatus shown in FIG. 1.

In such a relative time display, it is possible to change a reference time in accordance with a predetermined operation. Specifically for example, by clicking on any one of the displayed thumbnails, the imaging time point of the clicked thumbnail can be set as a reference for relative time. In a textual information 28b' in FIG. 4, for example, the reference for relative time (time "00:00:00") is changed to an imaging time point of thumbnail 28a-n as a result of clicking on the thumbnail 28a-n.

With a relative time display for each thumbnail, the observer and the like can estimate an intra-subject-imaging position of the thumbnail of interest. Specifically, when images capturing the diseased region and the like are observed based on a reference imaging time point of an intra-subject image capturing the small intestine, for example, the position of the diseased region can be calculated based on the start position of capturing the small intestine, and the relative time of the image capturing the diseased region.

The information content to be displayed as the textual information 28b or 28b' in the display sub-area 28 is variable according to a predetermined operation. It is also possible to hide the textual information 28b or 28b'. The display sub-area 28 includes lines which associate thumbnails and imaging time points of the thumbnails shown on the time bar 27, respectively.

Since there is a limitation in the display area available for the display sub-area 28, a batch display with up to a predetermined number of thumbnails 28a can be allowed. FIG. 3, for example, illustrates a case where a batch display with up to five thumbnails is allowed. When the number of extracted thumbnails 28a is greater than the predetermined number for the batch display, thumbnails over the predetermined number replace currently displayed thumbnails and are displayed in response to the operation of the scroll bar 28c displayed in the display sub-area 28. Each thumbnail displayed in the display sub-area 28 is displayed as the main display image 23 in response to the predetermined button operation or mouse operation.

Figure 5:
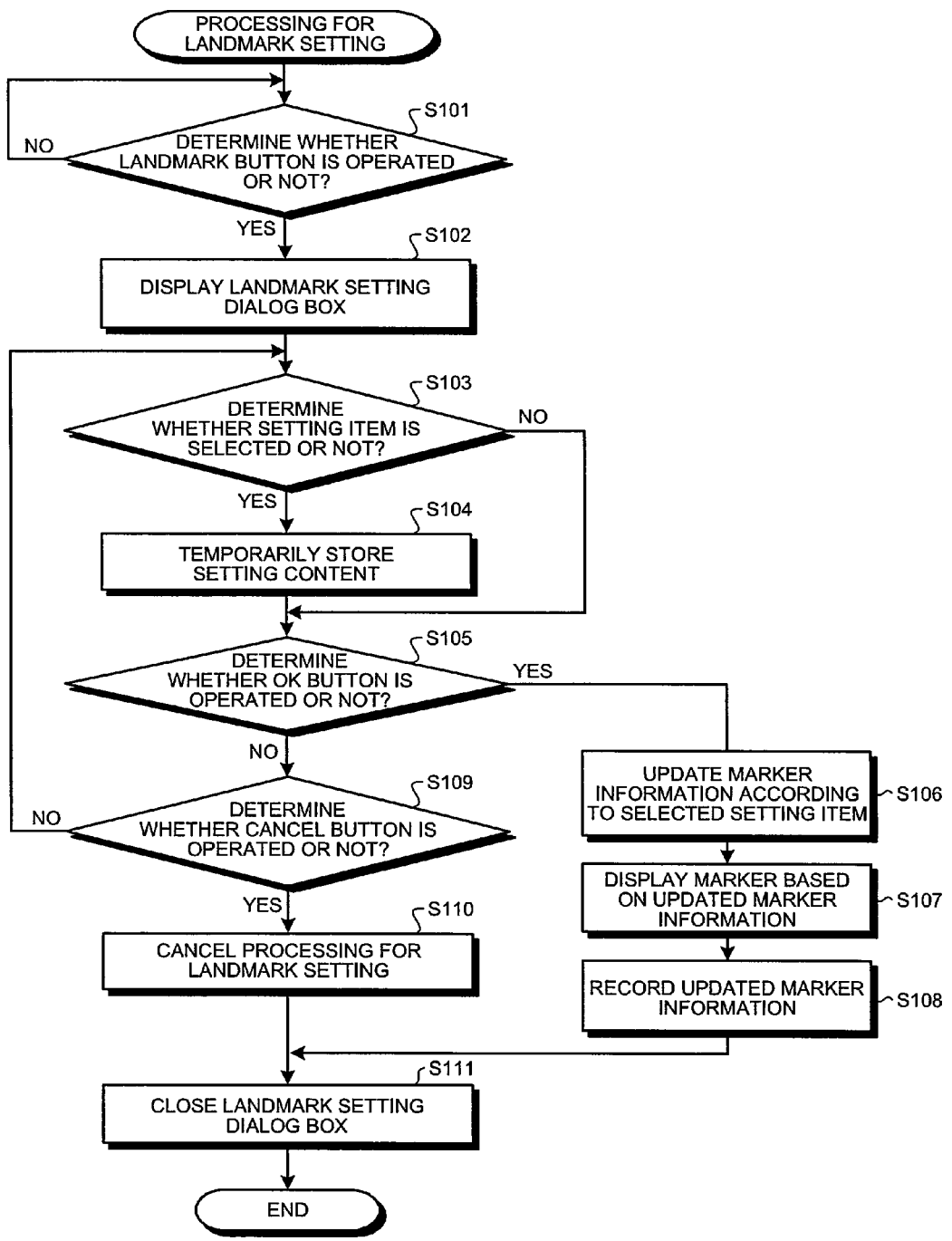
FIG. 5 is a flowchart of a procedure of a landmark setting operation to be performed by the image display apparatus shown in FIG. 1.

Here, a procedure for setting a landmark will be explained. The procedure is for displaying the marker on the time bar 27 in the image display apparatus 4 according to the first embodiment. FIG. 5 is a flowchart of the procedure for setting a landmark. As shown in FIG. 5, the image processing controller 15b determines whether a landmark button 29 is operated or not (step S101) to start the processing for the landmark setting. When the landmark button 29 is not operated ("No" at step S101), the determination processing is repeated in a predetermined cycle.

When the landmark button 29 is operated ("Yes" at step S101), the image display controller 15a displays a landmark setting dialog box for acquiring the detail of the marker information (step S102). At step S102, the image display controller 15a controls to display a landmark setting dialog box 30 so as to override the window 21, for example as shown in FIG. 6.

Figure 6:
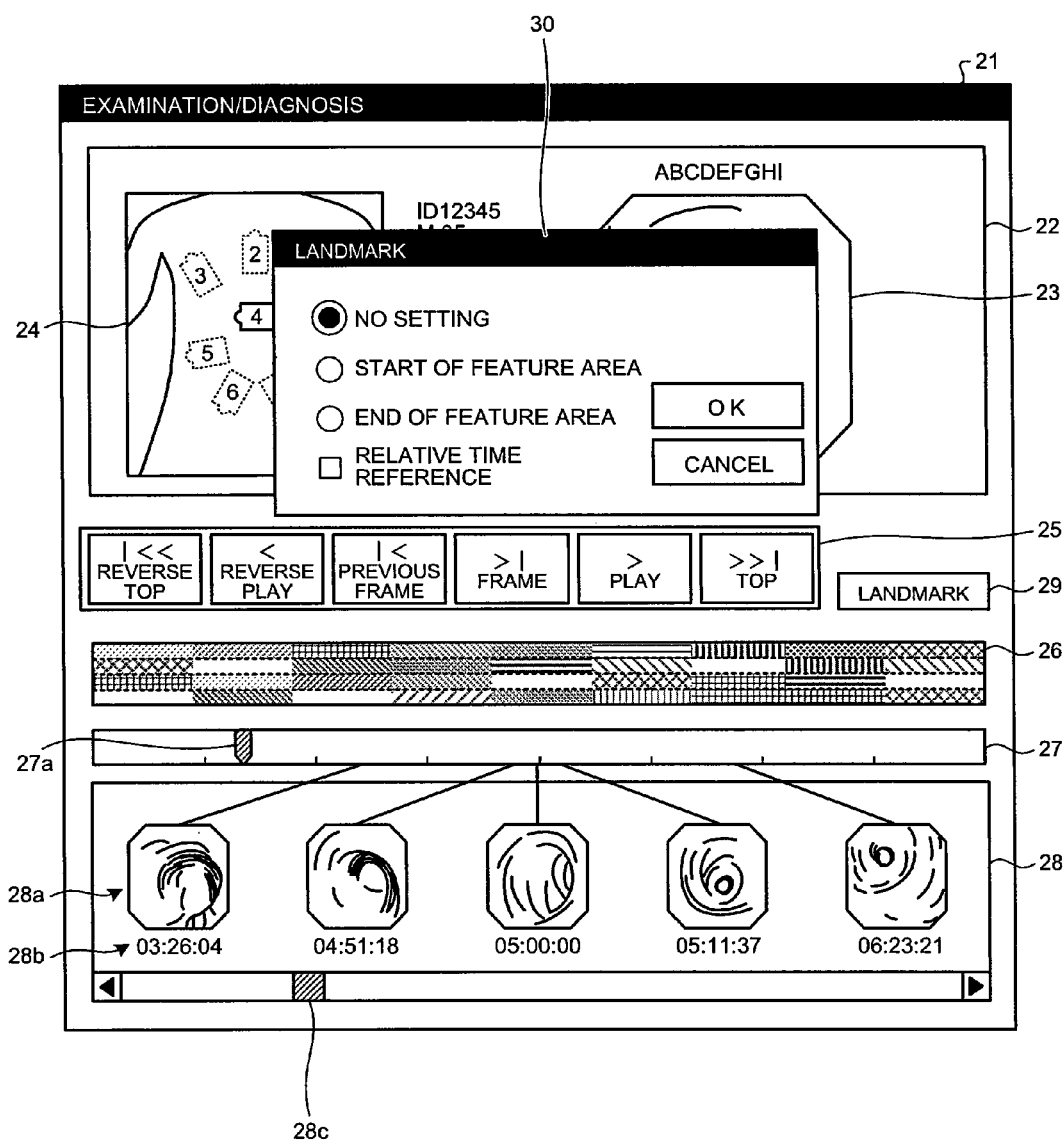
FIG. 6 is a diagram illustrating still another display screen image of the image display apparatus shown in FIG. 1.

In the landmark setting dialog box 30 shown in FIG. 6, "START OF FEATURE AREA" as an item for setting marker information which designates a start time point of the marker shown on the time bar 27, "END OF FEATURE AREA" as an item for setting mark information which designates an end time point thereof, "NO SETTING" as an item for performing no setting, and "RELATIVE TIME REFERENCE" as an item for setting a reference for relative time which is appended to the thumbnail 28a as the textual information are present to allow a selection of any one of the items.

In the landmark setting dialog box 30, "OK" button for confirming the selected item, and "CANCEL" button for cancelling the setting operation with the landmark setting dialog box 30 are present. When the "OK" button or "CANCEL" button is operated, the landmark setting dialog box 30 is closed automatically after a predetermined processing.

Next, the image display controller 15a determines whether any setting item is selected on the landmark setting dialog box 30 or not (step S103). When any item is selected ("Yes" at step S103), settings of the selected item are temporarily stored (step S104). On the contrary, when any item is not selected ("No" at step S103), the process goes to step S105. The determination processing at step S103 may preferably be performed in a predetermined time passage after the execution of step S102.

The image display controller 15a then determines whether the "OK" button is operated on the landmark setting dialog box 30 or not (step S105). When the "OK" button is operated ("Yes" at step S105), marker information is updated depending on the selected setting item (step S106) and the marker based on the updated marker information is displayed on the time bar 27 (step S107). Then, the updated marker information is recorded in the storage unit 14 (step S108) to move to step S111.

On the contrary, when the "OK" button is not operated ("No" at step S105), the image display controller 15a determines whether the "CANCEL" button is operated on the landmark setting dialog box 30 or not (step S109). When the "CANCEL" button is not operated ("No" at step S109), the processing from step S103 is repeated. When the "CANCEL" button is operated ("Yes" at step S109), every processing for the landmark setting is cancelled (step S110), the landmark setting dialog box 30 is closed (step S111), and the series of landmark setting processing ends.

Figure 7:
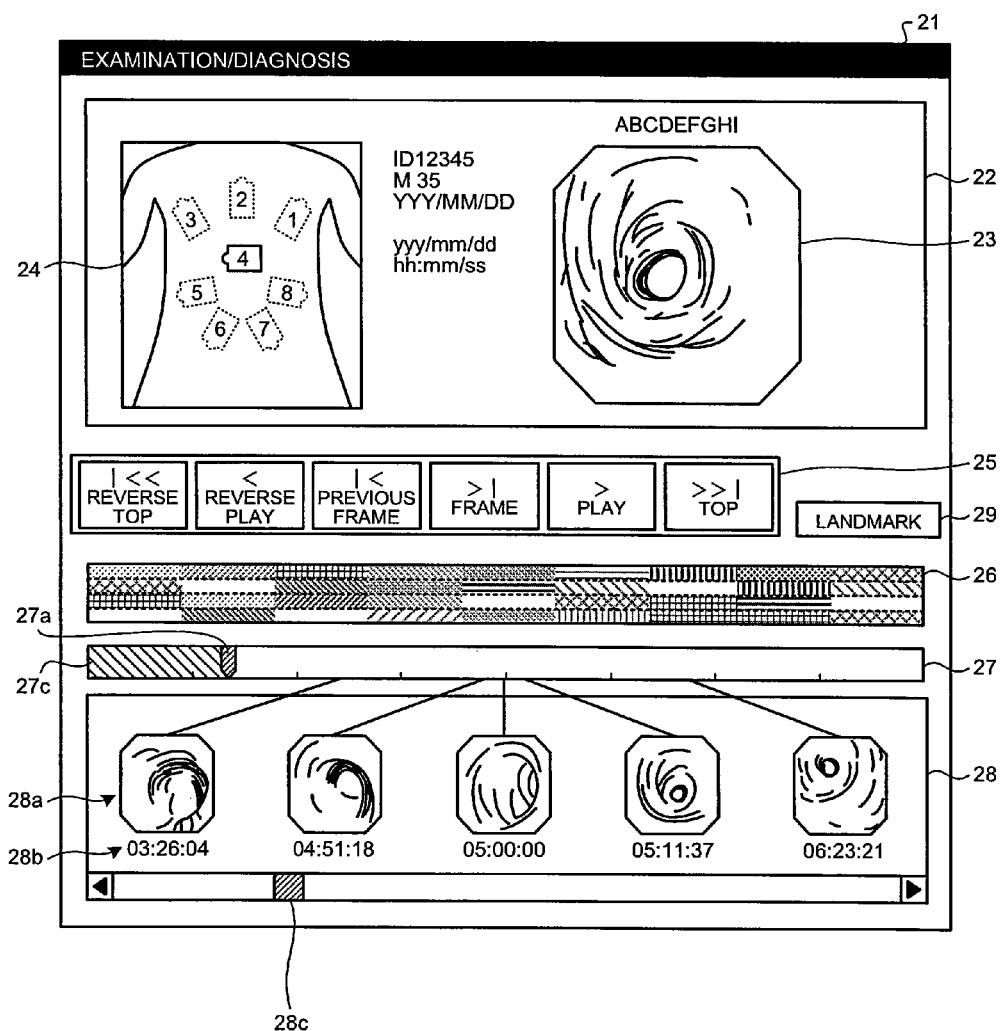
FIG. 7 is a diagram illustrating still another display screen image of the image display apparatus shown in FIG. 1.

At step S107, when the selected item on the landmark setting dialog box 30 is "START OF FEATURE AREA", and there is no other intra-subject images associated with marker information in the series of intra-subject images, the image display controller 15a, for example as shown in FIG. 7, marks the display area before the imaging time point of the intra-subject image which is newly associated with marker information on the time bar 27 with a marker 27c.

Figure 8:
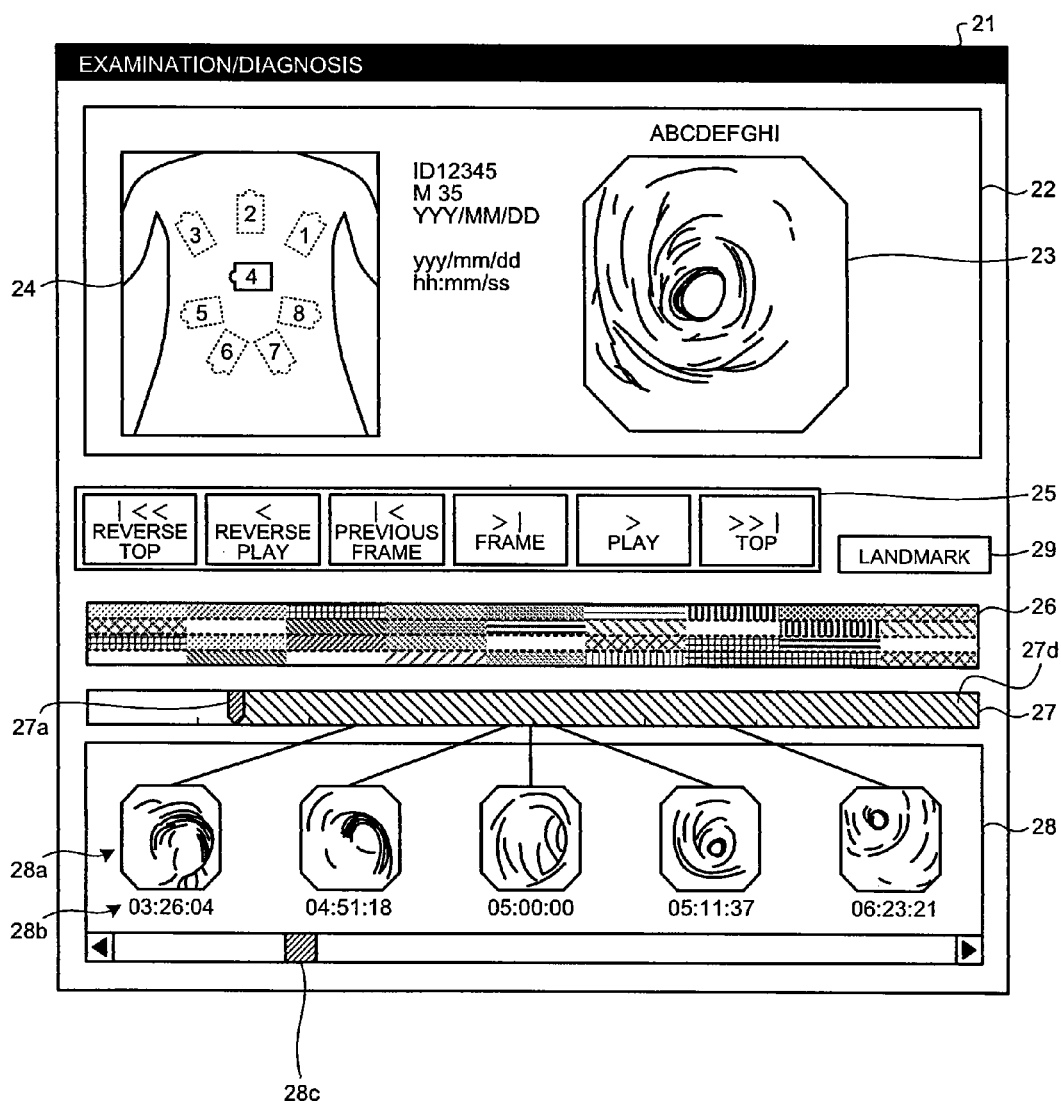
FIG. 8 is a diagram illustrating still another display screen image of the image display apparatus shown in FIG. 1.

At step S107, when the selected item is "END OF FEATURE AREA", and there is no other intra-subject images associated with marker information in the series of intra-subject images, the image display controller 15a, for example as shown in FIG. 8, marks the display area after the imaging time point of the intra-subject image which is newly associated with marker information on the time bar 27 with a marker 27d.

At step S107, when the selected item is "START OF FEATURE AREA" (or "END OF FEATURE AREA"), and there is an intra-subject image associated with marker information which indicates an end time point (or a start time point) in the series of intra-subject images, the image display controller 15a, for example as shown in FIG. 3, marks the display area between respective pieces of marker information on the time bar 27 with the marker 27b.

As explained above, in the image display apparatus 4 according to the first embodiment, the markers 27b to 27d and the like each indicating an imaging period of a group of images which is recognized as an image of interest are present on the time bar 27 indicating the imaging period of the series of intra-subject images. Such markers are displayed so as to be discriminable from the other display areas on the time bar 27. Thus, the observer or the like can easily recognize the imaging period where images of interest are present, and thereby reducing the time and effort for searching images of interest in every observation and resulting in realizing effective observation of the images of interest.

In the first embodiment described above, the series of images displayed in the image display apparatus 4 according to the present invention are explained as the series of intra-subject images which are captured by using the capsule endoscope 2 inserted into the subject 1. However, it is not necessarily limited to the intra-subject images, and may be any images of any subject as long as a series of images are captured at multiple time points by using any imaging device.

Second Embodiment

Next, a radio system for acquiring intra-subject information including an image display apparatus according to a second embodiment will be explained. The image display apparatus in this radio system for acquiring intra-subject information has a function as a filing device which stores patient information constituting of multiple kinds of information for specifying the subject (subject person, patient, and the like) in a storage unit as a database.

Figure 9:
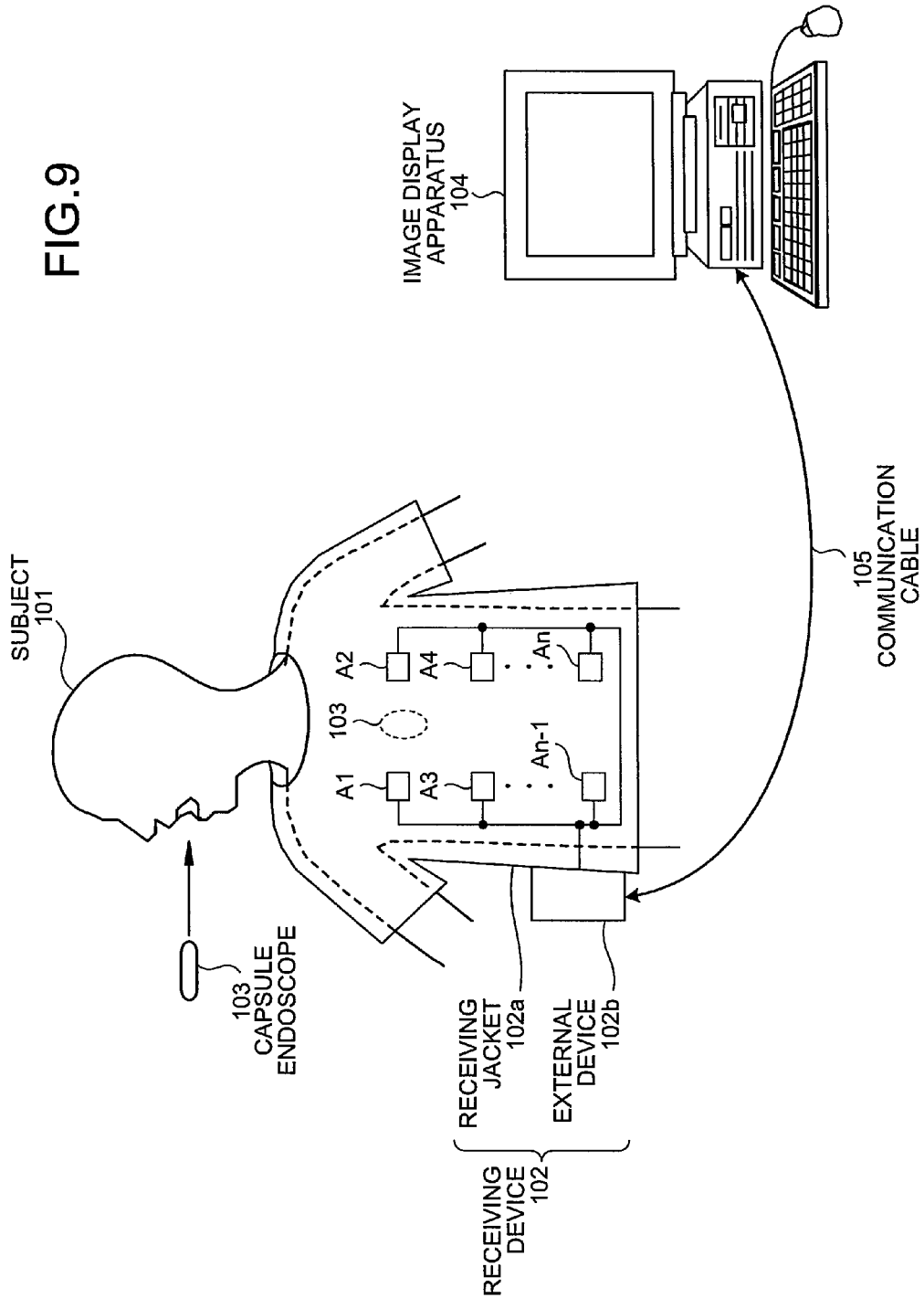
FIG. 9 a schematic diagram of an entire configuration of a radio system for acquiring intra-subject information according to a second embodiment.

FIG. 9 is a schematic diagram of an entire configuration of the radio system for acquiring intra-subject information according to the second embodiment. The radio system for acquiring intra-subject information uses a capsule endoscope as one example of a body-insertable device. In FIG. 9, the radio system for acquiring intra-subject information includes a receiving device 102 which has a radio receiving function, a capsule endoscope (body-insertable device) 103 which is inserted into a subject 101, captures images inside the body cavity, and transmits data such as an image signal to the receiving device 102. The radio system for acquiring intra-subject information further includes an image display apparatus 104 which displays a body cavity image based on the image signal received by the receiving device 102, and a communication cable 105 which transfers data between the receiving device 102 and the image display apparatus 104. The receiving device 102 includes a receiving jacket 102a which is worn by the subject 101, and an external device 102b which performs processing and the like of radio signals received via a plurality of antennas A1 to An attached to the receiving jacket 102a.

The image display apparatus 104 displays a body cavity image (which may be referred to also as an intra-subject image) captured by the capsule endoscope 103, and has a configuration like a work station which displays an image based on data obtained from the receiving device 102 via the communication cable 105. Specifically, the image display apparatus 104 may be configured to display directly on a CRT display, liquid crystal display, and the like, or may be configured to output an image to other media.

The communication cable 105 is normally detachable with respect to the external device 102b and the image display apparatus 104. The external device 102b is configured to be capable of inputting/outputting or recording data information when the communication cable 105 is connected to both of the external device 102b and the image display apparatus 104. In the second embodiment, when the receiving device 102 is initialized, for example, when old data such as image data stored in the storage unit in the receiving device 102 in a previous examination is deleted, or patient information is registered, the communication cable 105 is connected to the external device 102b and the image display apparatus 104 to transmit data (e.g., patient information of a subject to be registered in the receiving device 102) from the image display apparatus 104 to the external device 102b. When the initialization is completed, the communication cable 105 is removed from the external device 102b and the image display apparatus 104 to make the external device 102b and the display apparatus 104 unconnected. While the capsule endoscope 103 travels inside the body cavity of the subject 101, the external device 102b and the display apparatus 104 are kept unconnected with each other.

The external device 102b receives and records data wirelessly transmitted from the capsule endoscope 103. After the capsule endoscope 103 is discharged from the subject 101, i.e., after the imaging of the inside of the subject 101 is finished, the communication cable 105 is connected between the external device 102b and the image display apparatus 104, so that the image display apparatus 104 reads out the data which is transmitted by the capsule endoscope 103 and recorded by the external device 102b. The communication between the external device 102b and the image display apparatus 104 according to the present invention is not limited to using the communication cable 105, and may be performed via wireless connection or may be performed by connecting the external device 102b and the image display apparatus 104 with a cradle capable of data synchronization. In this case, the image display apparatus 104 and the cradle are connected through the communication cable, the external device 102b is disposed on the cradle, and then data transfer is performed between the external device 102b and the image display apparatus 104. Patient information is an example of identification information of the patient, and includes information such as an examination ID like an examination date, a name, an age, and a sex of the patient.

Figure 10:
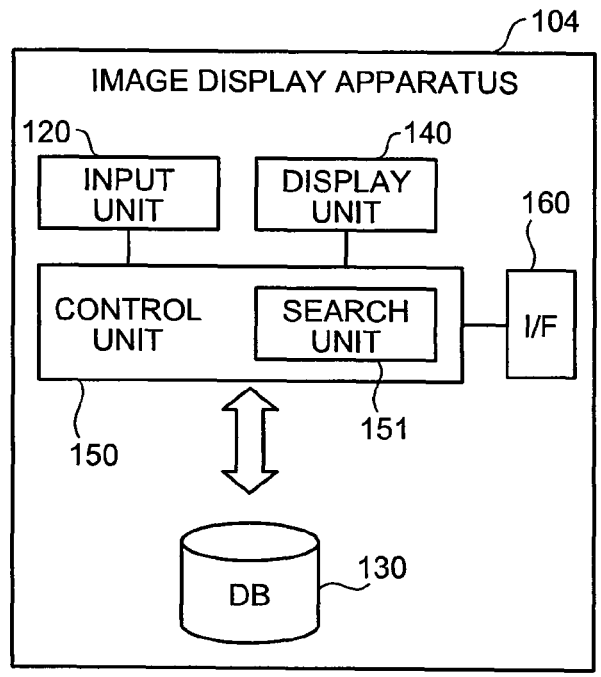
FIG. 10 is a schematic block diagram of a configuration of a display apparatus according to a second embodiment.

Next, the configuration of the image display apparatus 104 according to the second embodiment of the present invention will be explained. FIG. 10 is a schematic block diagram of the configuration of the image display apparatus 104 according to the second embodiment. In FIG. 10, the image display apparatus 104 includes an input unit 120 as an input unit; a database (abbreviated as DB in the following when appropriate) 130 as a storage unit; a display unit 140 as a display unit; a control unit 150; and an interface (abbreviated as I/F in the following when appropriate) 160 as a communication connecting unit with other equipment, and has a function of filing data information such as patient information and image information.

The input unit 120 realized by a pointing device such as a keyboard and a mouse inputs information for instructing the operation of the image display apparatus 104 and the processing to be performed by the image display apparatus 104, and transmits the instruction information to the control unit 150. The input unit 120 also inputs selection-information for selecting a desired image from images displayed in a display area of the display unit 140. For example, when the mouse as the input unit 120 is operated to move a cursor displayed on the screen to the image displayed in the display area of the display unit 140, and the desired image is clicked on, the input unit 120 inputs instruction information as selection-information for selecting the desired image.

The input unit 120, for example by operating the keyboard, inputs patient information necessary for initialization of the receiving device 102, such as an examination ID, name, age, and sex of the patient, and the like, and transmits the patient information to the control unit 150. When the input unit 120 searches the patient information or case data stored in the database 130, the input unit 120 inputs one piece of the patient information, for example, patient name to be transmitted to a search unit 151 of the control unit 150 described later. Here, "case data" means various types of data related to the subject 101, a group of images of whose interior is captured by the capsule endoscope 103 or the like. The case data includes, for example, patient information of the subject 101, a series of intra-subject images, diagnosis data such as a result of diagnosis of the subject 101.

The database 130 realized by a hard disc device and the like, for example, is capable of retaining various images and the like, storing patient information transmitted from the input unit 120, searching and reading of the information by the search unit 151. The database 130 stores patient information of plural subjects and case data of one or more subjects in a readable manner.

The display unit 140 realized by the CRT display, liquid crystal display, and the like displays instruction information from the input unit 120 or instruction results. The display unit 140 displays patient information input by the input unit 120 and patient information or case data searched by the search unit 151 based on one piece of patient information input by the input unit 120. In this case, the display unit 140 further displays, for example, a body cavity image of a group of images stored in the database 130, reduced-scale images (thumbnails) instructed by the instruction information, and the like.

The control unit 150 controls processing and operation of the input unit 120, the database 130, and the display unit 140 each. The control unit 150 includes the search unit 151 which searches patient information or case data stored in the database 130. The search unit 151 searches relevant patient information or case data from patient information or case data stored in the database based on one piece of information included in the patient information, such as information on the patient name, input by an operation of the keyboard as the input unit 120 performed by a user such as a doctor. The control unit 150 displays the patient information or the case data found as a result of search on the display unit 140. When there are plural patients having the same name, a plural pieces of patient information for plural patients are searched and displayed, so that the user can select, by operating the mouse of the input unit 120, the relevant patient information of the subject to be actually examined. When case data of plural subjects having the same name is stored in the database 130, the search unit 151 searches case data of plural subjects matching a search key (such as a patient name), and the control unit 150 makes the display unit 140 display a list of case data of the plural subjects found by the search unit 151, so that the user can select the case data of an examined subject from the list of case data by manipulating the mouse of the input unit 120. The information to be a search key for the patient information or the case data is not limited to name, and may be any one piece of information other than the patient name of the patient information, for example, an age.

The interface 160 is an input/output interface for connecting the image display apparatus 104 and another device, the receiving device 102, for example. When the interface 160 is connected to the receiving device 102 by the communication cable 105 or the like mentioned above for communication, the interface 160 works as a communication unit which transmits the patient information of the subject to be registered in the receiving device 102 to the receiving device 102 under the control of the control unit 150. The patient information of the subject transmitted to the receiving device 102 through the interface 160 is registered in the external device 102b of the receiving device 102.

Figure 11:
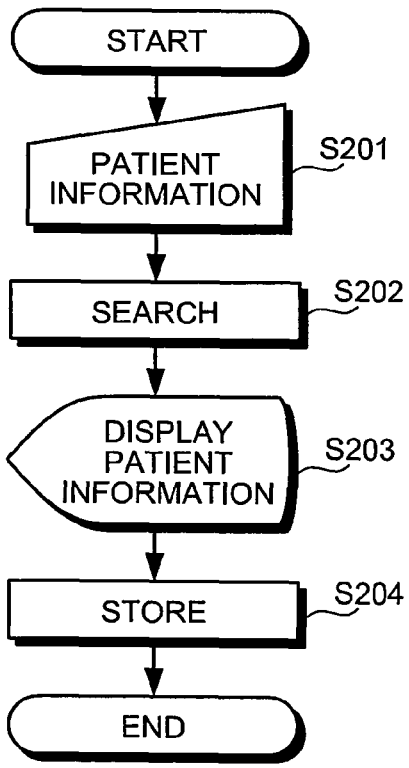
FIG. 11 is a flowchart for explaining a search operation of patient information performed by the display apparatus according to the second embodiment.

Next, an operation for searching patient information in the image display apparatus 104 will be explained with reference to the flowchart in FIG. 11. FIG. 11 is a flowchart for explaining a search operation of patient information performed by the image display apparatus 104 according to the second embodiment. In FIG. 11, when the user such as a doctor operates the keyboard of the input unit 120 and completes inputting one piece of the patient information, for example, patient name information (step S201), the search unit 151 searches the database 130 for patient information based on the input patient name (step S202).

Then, when the search unit 151 searches the relevant patient information, the patient information as the search result is displayed in the display area of the display unit 140 (step S203). When there is no relevant patient name input, all pieces of patient information including the patient name, age, sex, examination ID, and the like are input and stored in the database 130 (step S204).

The image display apparatus 104 electrically connected to the external device 102b of the receiving device 102 through the communication cable 105, performs a data synchronization between the external device 102b and the image display apparatus 104 to enable a data transfer. The external device 102b includes a hard disc (not shown) as an internal storage medium. Before the examination, the external device 102b and the image display apparatus 104 are connected through the communication cable 105, and the searched patient information is transferred from the image display apparatus 104 working as the work station to the external device 102b to be stored in the hard disc of the external device 102b. Then, the external device 102b registers the patient information of the examined subject in an internal storage medium.

While the capsule endoscope 103 travels inside the body cavity of the subject 101, the communication cable 105 is removed from the external device 102b, and then the external device 102b is attached to the subject 101 to record data transmitted from the capsule endoscope 103. After imaging of the inside of the subject 101 is finished, the external device 102b is again connected to the image display apparatus 104 through the communication cable 105, and the image display apparatus 104 reads out data (image information) recorded in the hard disc of the external device 102b.

On the other hand, in the image display apparatus 104 which takes in the group of body cavity images of the subject 101 from the external device 102b, the control unit 150 makes the case data including the patient information identifying the subject 101 and the group of body cavity images stored in the database 130. The process is repeated so that the database 130 stores case data of plural subjects. The control unit 150 makes the display unit 140 display case data found as a result of search by the search unit 151 from plural pieces of case data stored in the database 130.

Next, a search operation performed in the image display apparatus 104 to search the case data of the subject will be explained. The control unit 150 follows substantially the same process procedures as the search process procedures of the patient information from step S201 to step S204 mentioned above, so as to search the database 130 for the case data of a subject matching a search key, and displays the searched case data on the display unit 140.

Specifically, at step S202 mentioned above, the search unit 151 searches the database 130 for the case data which includes a search key (such as a patient name which is an example of information included in the patient information) input by the input unit 120 as a part of data. When plural pieces of case data stored in the database 130 include the search key, the search unit 151 searches plural matching pieces of case data.

On the other hand, in step S203 mentioned above, the control unit 150 displays the case data searched by the search unit 151 on the display unit 140. In this case, the control unit 150 displays the intra-subject images, patient information, and the like included in the case data on the display unit 140 as shown in FIG. 3, for example. When the search unit 151 finds plural pieces of case data as matches in step S202, the control unit 150 displays a list of plural pieces of case data found by the search unit 151 on the display unit 140, and also displays information and a GUI on the display unit 140 to instruct to select the case data of the examined subject from the list. The input unit 120 inputs selection-information of the case data based on a manipulation by the user to the control unit 150. The control unit 150 selects the case data corresponding to the input selection-information from the list, and displays the intra-subject images, patient information, and the like included in the selected case data on the display unit 140.

The control unit 150 has an image processing function similar to that of the control unit 15 of the image display apparatus 4 according to the first embodiment described above. The control unit 150 generates a thumbnail mentioned above based on instruction information input by the input unit 120, and additionally displays the generated thumbnail on the display unit 140. The control unit 150 makes the thumbnail data included in the case data. Further, when the diagnosis data such as a result of diagnosis of the subject is input by the input unit 120, the control unit 150 makes the input diagnosis data included in the case data of the subject. The control unit 150 updates the case data in the database 130 with the case data including the newly generated thumbnail data, diagnosis data, and the like in step S204 mentioned above.

The control unit 150 can display all pieces of data in the case data on the display unit 140 based on a instruction information input by the input unit 120. Specifically, when the thumbnail data, the diagnosis data, and the like are included in the case data in addition to a series of intra-subject images and the patient information, the control unit 150 can display the thumbnail and the diagnosis data in addition to the series of intra-subject images and the patient information on the display unit 140.

In the second embodiment, since the search unit 151 searches the database 130 for the entirety of the relevant patient information at a stage where one piece of patient information is input and then controls to display the search result on the display unit 140, and to transmit the searched patient information to the receiving device 102 via the interface 160. Therefore, patient information of a target subject can be quickly retrieved from the database 130 storing patient information of plural subjects, and the retrieved patient information can be easily registered in the receiving device of the group of intra-subject images. As a result, a labor of inputting the patient information at the registration of the patient information to the receiving device can be saved.

Further, in the second embodiment, the search unit 151 searches the database 130 for the case data of the subject including one piece of input information at a stage where the one piece of patient information is input, and_then the searched case data of the subject is displayed on the display unit 140. Therefore, case data of a target subject can be quickly retrieved from the database 130 storing data group including a group of intra-subject_images, patient information, and the like. As a result, data concerning the subject such as a series of intra-subject images, patient information, results of diagnosis, and the like included in the case data of the examined subject can be quickly output and displayed.

Modification

In the second embodiment, patient information or case data is searched at the stage where the user completes inputting one piece of the patient information. However, the search unit 151 may start searching in the middle of inputting one piece of the patient information, i.e., at a time when a part of one piece of the patient information is input. In the modification, patient information or case data including the patient information of a patient family name which is the same as the name previously searched right before the current search is controlled to be displayed on the display area of the display unit 140 by searching the database 130 at a time when the family name of the patient full name is input by the input unit 120. The patient information and the case data in the database 130 is appended with history information indicating the date of searching the patient information, for example.

Figure 12:
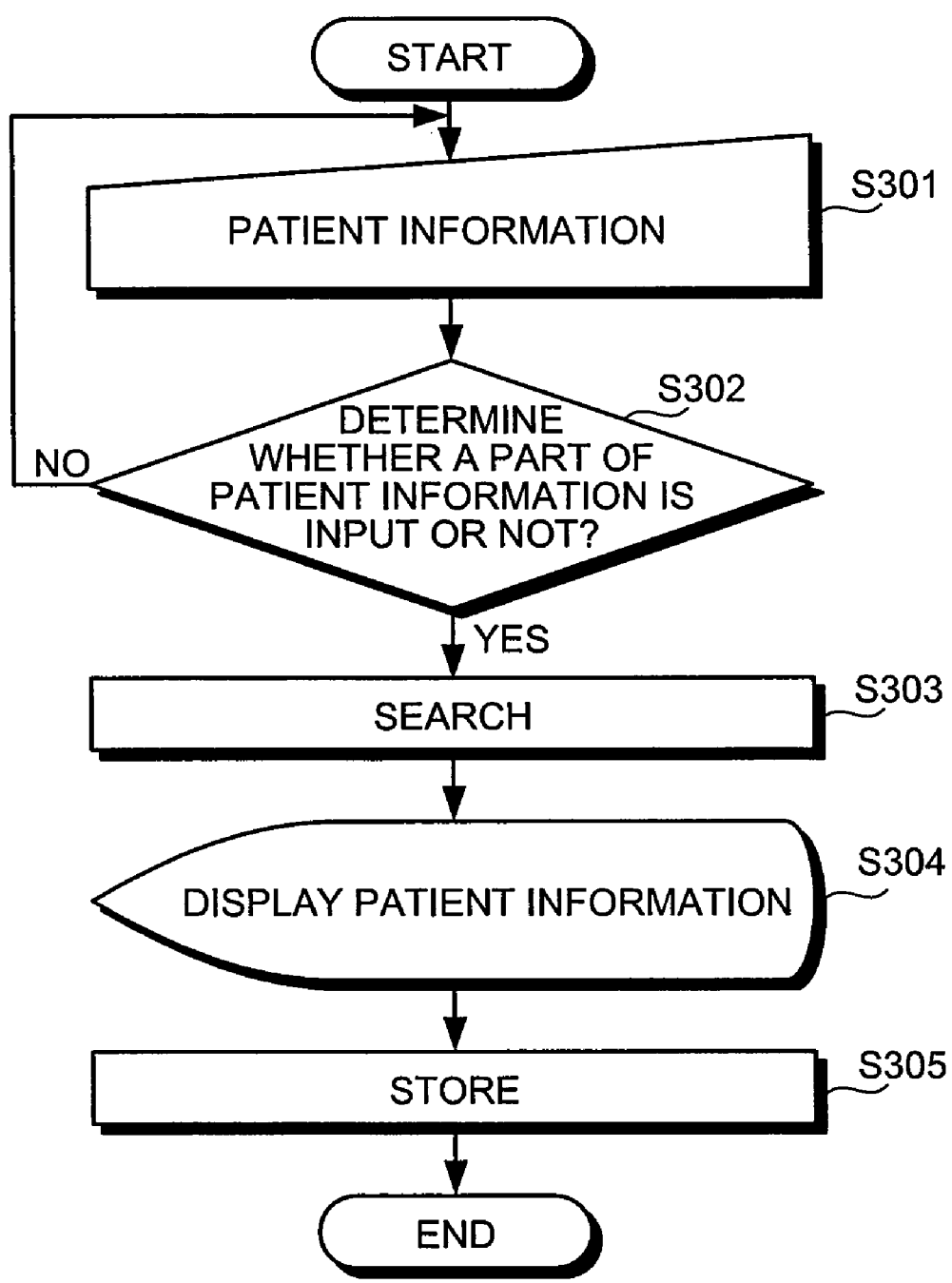
FIG. 12 is a flowchart for explaining a search operation of patient information performed by a display apparatus according to a modification of the second embodiment.

FIG. 12 is a flowchart of the modification of the second embodiment for explaining a search operation of patient information in the image display apparatus 104. In this modification, a case where patient information or case data of a patient named "Hanako Yamada" is, for example, searched will be explained (the same is applied to the other embodiments to be described below).

In FIG. 12, when the user inputs one piece of patient information "Hanako Yamada" by operating the keyboard of the input unit 120 (step S301), the search unit 151, at a time when "Yamada" is input (Yes in step S302), searches the database 130 for patient information which includes "Yamada" and is searched right before the current search based on history information (step S303), and displays the searched patient information in the display area of the display unit 140 (step S304). If no such search key is input (No in step S302), process procedures return to step S301. In the modification, when there is no relevant patient name "Hanako Yamada", all pieces of patient information including the patient name, age, sex, examination ID, and the like are input and stored in the database 130 (step S305).

Next, a search operation performed in the image display apparatus 104 according to the modification of the second embodiment to search case data of the subject will be explained. In the modification of the second embodiment, the control unit 150 follows substantially the same process procedures as the search process procedures of the patient information from step S301 to step S305 mentioned above, so as to search the database 130 for the case data of a subject based on a search key, i.e., a part of the patient information, and displays the searched case data on the display unit 140.

Specifically, at step S303 mentioned above, the search unit 151 searches the database 130 for the case data which includes a search key (e.g., a part of the name of the subject included in the patient information, such as "Yamada") input by the input unit 120 as a part of data. When plural pieces of case data stored in the database 130 include the search key, the search unit 151 searches plural matching pieces of case data.

On the other hand, in step S304 mentioned above, the control unit 150 makes the display unit 140 display the case data found as a result of search by the search unit 151. In this case, the control unit 150 displays the intra-subject images, patient information, and the like included in the case data on the display unit 140 as shown in FIG. 3, for example. When the search unit 151 finds plural pieces of case data as matches in step S303, the control unit 150 displays a list of plural pieces of case data found by the search unit 151 on the display unit 140, and also displays information and GUI on the display unit 140 to instruct to select the case data of the examined subject from the list. Thereafter, case data corresponding to the selection-information input by the input unit 120 is selected from the list, and the display unit 140 displays the intra-subject images, patient information, and the like included in the selected case data.

Further, when at least one of the thumbnail and the diagnosis data concerning the case data is generated, the control unit 150 updates the case data in the database 130 with the case data including the newly-generated thumbnail data, diagnosis data, and the like in step S305 mentioned above. The control unit 150 can display the series of intra-subject images, patient information, thumbnail, and diagnosis data included in the case data searched from the database 130 on the display unit 140.

In this modification of the second embodiment as described, since the search unit 151 searches the database 130 for relevant patient information at the time when at least a part of one piece of patient information is input, and then controls to display the search result on the display unit 140, and controls to transmit the searched patient information to the receiving device 102 through the interface 160. Therefore, patient information of a target subject can be quickly retrieved from the database 130 storing patient information of plural subjects, and a labor of inputting the patient information can be saved at the registration of the patient information of the subject to the receiving device of the group of intra-subject images.

Further, in this modification of the second_embodiment, the search unit 151 searches the database 130 for relevant case data of a subject including the input piece of patient information at the time when at least a part of the piece of patient information is input, and then controls to display the searched case data of the subject on the display unit 140. Therefore, case data of a target subject can be more quickly retrieved from the database 130, and data concerning the subject such as a series of intra-subject images, patient information, diagnosis result, and the like included in the case data of an examined subject can be more quickly output and displayed.

Third Embodiment

Figure 13:
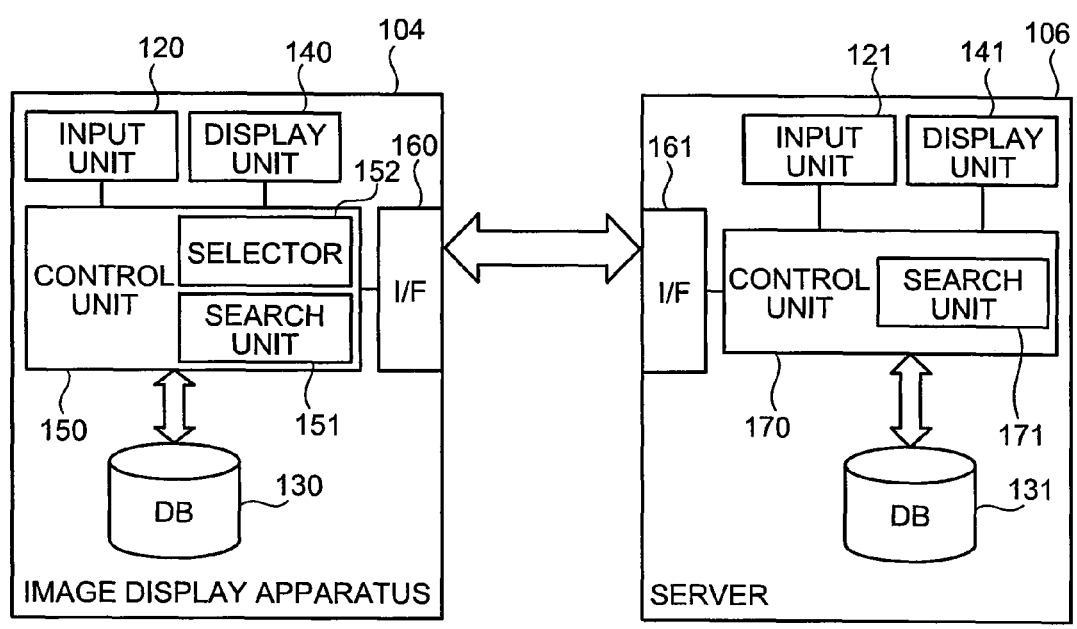
FIG. 13 is a schematic block diagram of a configuration of a filing system according to a third embodiment.

FIG. 13 is a schematic block diagram of a configuration of a filing system including an image display apparatus according to a third embodiment. In FIG. 13, an image display apparatus 104 according to the third embodiment is different from the image display apparatus according to the second embodiment in that a selector 152 is provided in the control unit 150 as a selector which selects a target database to be searched for patient information or case data when there are a plurality of databases in a system, and that the image display apparatus is connected to a server 106, which stores data concerning the subject such as patient information as case data, via the interface 160.

In the filing system according to the third embodiment, the image display apparatus 104 constitutes a second filing device, and the server 106 constitutes a first filing device. The image display apparatus 104 includes the input unit 120 as a second input unit having the same function as in the image display apparatus according to the second embodiment; the database 130 as a second storage unit; the display unit 140 as a second display unit; the control unit 150; the search unit 151 as a second search unit; and the interface 160, other than the selector 152. The selector 152 selects a database which is searched for patient information or case data with respect to the database 130 in the image display apparatus and a database 131 in the server 106. In the third embodiment, the database 130 in the image display apparatus having a higher hit rate in information search is selected first, and the database 131 is then selected when there is no relevant patient information or case data found in the database 130.

The server 106 includes an input unit 121 as a first input unit having the same function as in the image display apparatus 104 according to the second embodiment; the database 131 as a first storage unit; a display unit 141 as a first display unit; a control unit 170; a search unit 171 as a first search unit; and an interface 161. When the selector 152 selects the database 131 as a target for search, the search unit 171 searches the database 131 for relevant patient information based on a part of one piece of the patient information input by the input unit 120 to output the search result of patient information to the image display apparatus 104 via the interface 161 (this is the same function as in the modification of the second embodiment). Even when patient information is input by the input unit 121, the search unit 171 searches database 131 for the relevant patient information based on a part of one piece of the patient information, and controls to display the search result of patient information or case data in the display area of the display unit 141.

In the image display apparatus 104 according to the third embodiment, the interface 160 is selectively connected to the receiving device 102 of the group of intra-subject images or to the external server 106 for communication. The interface 160 works as a communication unit that transmits/receives data between the image display apparatus 104 and the receiving device 102 when connected to the external device 102b of the receiving device 102 via the communication cable 105 or the like for communication, and serves as a communication unit that transmits/receives data between the image display apparatus 104 and the server 106 when connected to the server 106 via the interface 161 of the server 106 or the like for communication.

Figure 14:
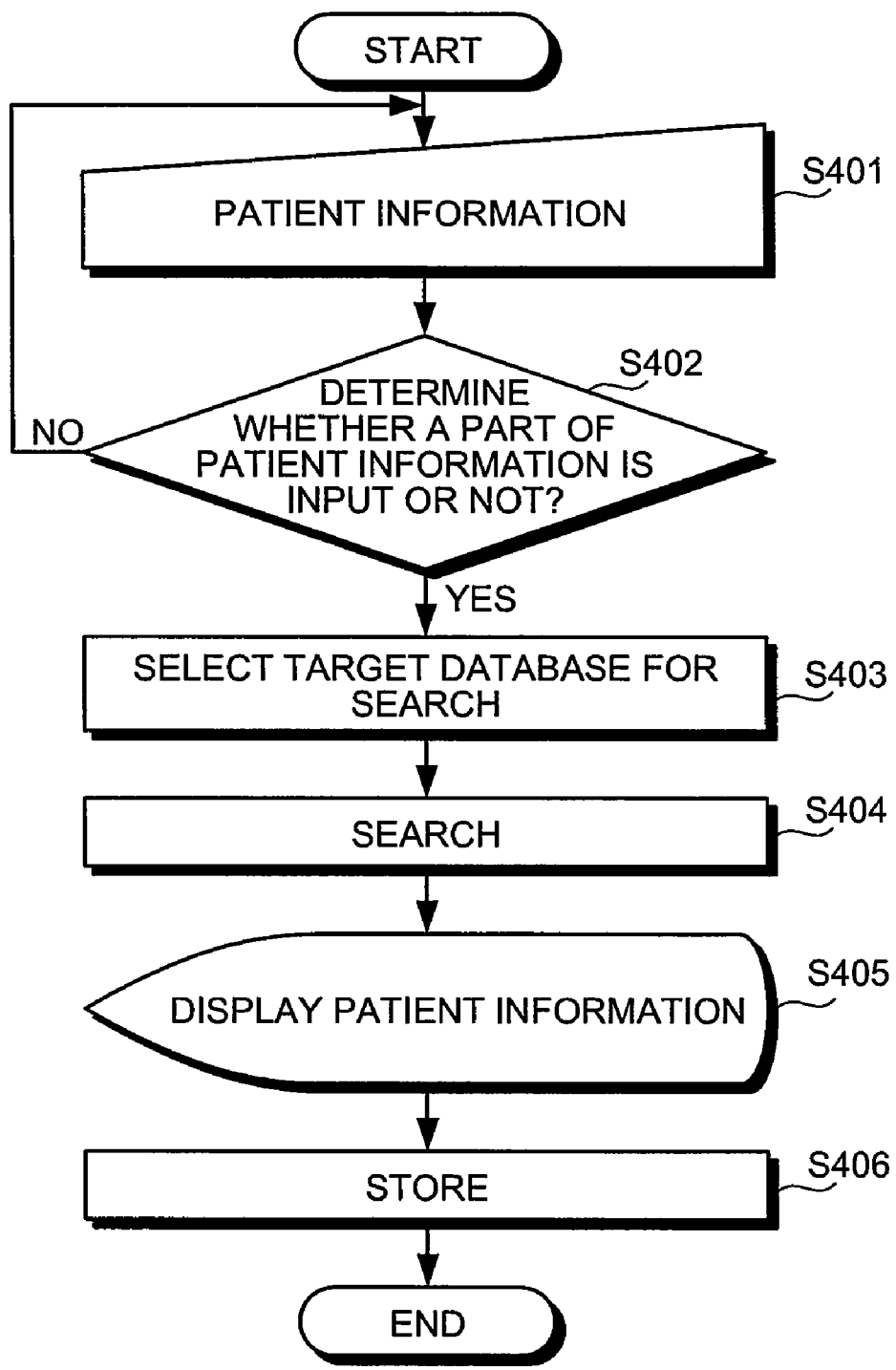
FIG. 14 is a flowchart for explaining a search operation of patient information performed by the filing system according to the third embodiment.

Next, an operation for searching patient information in a filing system according to the third embodiment will be explained with reference to the flowchart in FIG. 14. FIG. 14 is a flowchart for explaining a search operation of the patient information in the filing system according to the third embodiment. In FIG. 14, when the user inputs one piece of patient information "Hanako Yamada" by operating the keyboard of the input unit 120 (step S401), the search unit 151, at a time when input of at least a part of information, such as "Yamada" is completed (Yes in step S402), the selector 152 selects the database 130 in the image display apparatus as a target for search (step S403). On the other hand, when such a search key is not input (No in step S402), the process procedures returns to step S401.

Next, in response to the selection of the database 130 by the selector 152, the search unit 151 searches the database 130 for patient information including the name of "Yamada", which is searched right before the current search, based on the history information (step S404), and displays the searched patient information in the display area of the display unit 140 (step S406) when the relevant patient information is found as a result of search (Yes in step S405).

Here, when the search unit 151 cannot find relevant patient information (No in step S405), the selector 152 selects the database 131 as a search target at step S403. Specifically, the selector 152 repeats the selection process of the search-target database until the search unit 151 finds relevant patient information for the search key. This selection-information of the database used by the selector 152 is transmitted to the server 106 via the interface 160. Then, in response to the selection of the database 131 by the selector 152, the search unit 171 of the server 106 searches the database selected based on the selection-information, i.e., the database 131 selected by the selector 152 for patient information including the name of "Yamada", which is searched right before the current search, based on the history information (step S404). When the relevant patient information is found from the database 131 (Yes in step S405), the control unit 170 transmits the search result of patient information to the image display apparatus 104 via the interface 161.

When the search unit 151 of the image display apparatus 104 retrieves the patient information thereby finishing the search process of the patient information, and the control unit 150 makes the searched patient information is displayed in the display area of the display unit 140 (step S406), and stores the patient information in the database 130 (step S407). In the third embodiment, when there is no relevant patient name "Hanako Yamada", the server 106 transmits the search result that there is no targeted information to the image display apparatus 104, for example, and then the control unit 150, based on the search result, controls to input all pieces of patient information such as the patient name, age, sex, examination ID, and the like and to store the information in the database 130 (step S407).

Next, a search operation performed in the image display apparatus 104 according to the third embodiment to search the case data of the subject will be explained. In the third embodiment, the control unit 150 follows substantially the same process procedures as the search process procedures of the patient information from step S401 to step S407 mentioned above, so as to select the database as a search target of the case data, search the case data of the subject based on a search key, i.e., at least a part of patient information, and display the searched case data on the display unit 140.

Specifically, when a search key, i.e., at least a part of patient information (such as "Yamada" of the subject name "Hanako Yamada") is input by the input unit 120, the selector 152 selects database as a search target of the case data in step S403, and repeats the selection process of the database until the search unit 151 finds relevant case data for the search key. The selector 152 first selects the database 130 in the image display apparatus 104 where information hit rate is high in the search process of case data. When the case data is not found in the database 130, the selector 152 selects the database 131 in the server 106.

On the other hand, in step S404 mentioned above, the search unit 151 searches the database (more specifically, the database 130 or 131) selected by the selector 152 for case data including a search key (e.g., a part of patient name in the patient information, such as "Yamada") input by the input unit 120 as a part of data. When the case data corresponding to the search key is stored in the database 130 of the apparatus (i.e., image display apparatus 104), the search unit 151 searches the database 130 for the relevant case data to finish the search process of the case data. On the other hand, when the case data corresponding to the search key is stored in the database 131 in the server 106, the search unit 171 of the server 106 searches the database 131 which is selected according to the selection-information from the selector 152 for the case data corresponding to the search key. The search unit 151 acquires the case data found through the search by the search unit 171 of the server 106 via the interface 160 to finish the search process of the case data. When plural pieces of case data including the search key are stored in each of the databases 130 and 131, the search units 151 and 171 search plural relevant pieces of case data.

In addition, in step S406 mentioned above, the control unit 150 displays the case data found as a result of search by the search unit 151 on the display unit 140. In this case, the control unit 150 displays intra-subject images, patient information, and the like included in the case data on the display unit 140 as shown in FIG. 3, for example. When the search unit 151 finds plural pieces of case data as a result of search in step S404 mentioned above, the control unit 150 displays a list of plural pieces of case data searched by the search unit on the display unit 140, and also displays information and a GUI on the display unit 140 to instruct to select the case data of the examined subject from the list, similarly to the case of patient information described above. Thereafter, case data corresponding to the selection-information input by the input unit 120 is selected from the list, and the display unit 140 displays the intra-subject images, patient information, and the like included in the selected case data.

Further, when at least one of the thumbnail and diagnosis data concerning the case data is generated, the control unit 150 updates the case data in the database 130 with the case data including newly-generated thumbnail data, diagnosis data, and the like in step S407 mention above. The control unit 150 can display the series of intra-subject images, patient information, thumbnail, diagnosis data, and the like included in the case data searched from the database 130 on the display unit 140. When the case data displayed on the display unit 140 is case data searched from the database 131 of the server 106, the control unit 150 stores the case data acquired from the server 106 in the database 130.

In the third embodiment as described, when there are a plurality of databases in the system, patient information of a target subject is searched from data group in the selected database after the selector selects a target database for search. Thus, it is possible to securely retrieve necessary patient information for the registration of patient information in the receiving device of the group of intra-subject images from the plurality of databases with the same advantages as in the second embodiment.

Further, in the third embodiment, when there are plural databases in the system, case data of a target subject is searched from data group in the selected database after the selector selects a target database for search. Thus, it is possible to securely retrieve necessary case data for the intra-body examination or the diagnosis of the subject from the plural databases with the same advantages as in the second embodiment. As a result, data concerning the subject such as a series of intra-subject images, patient information, diagnosis result, and the like included in the case data of the examined subject can be quickly and securely output and displayed.

Fourth Embodiment

Figure 15:
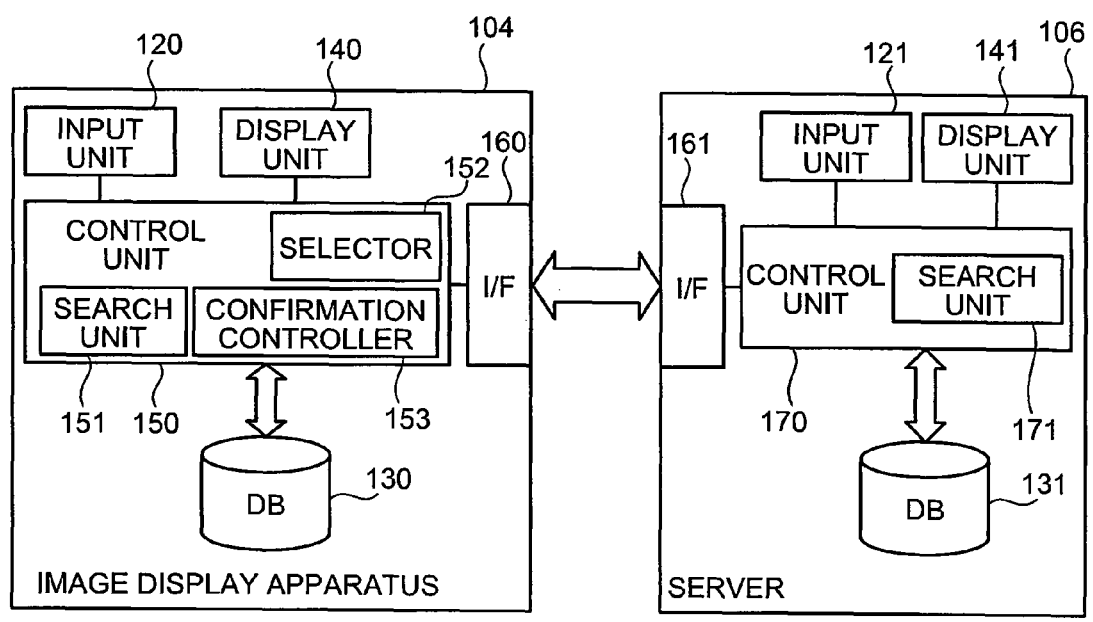
FIG. 15 is a schematic block diagram of a configuration of a filing system according to a fourth embodiment.
Figure 16:
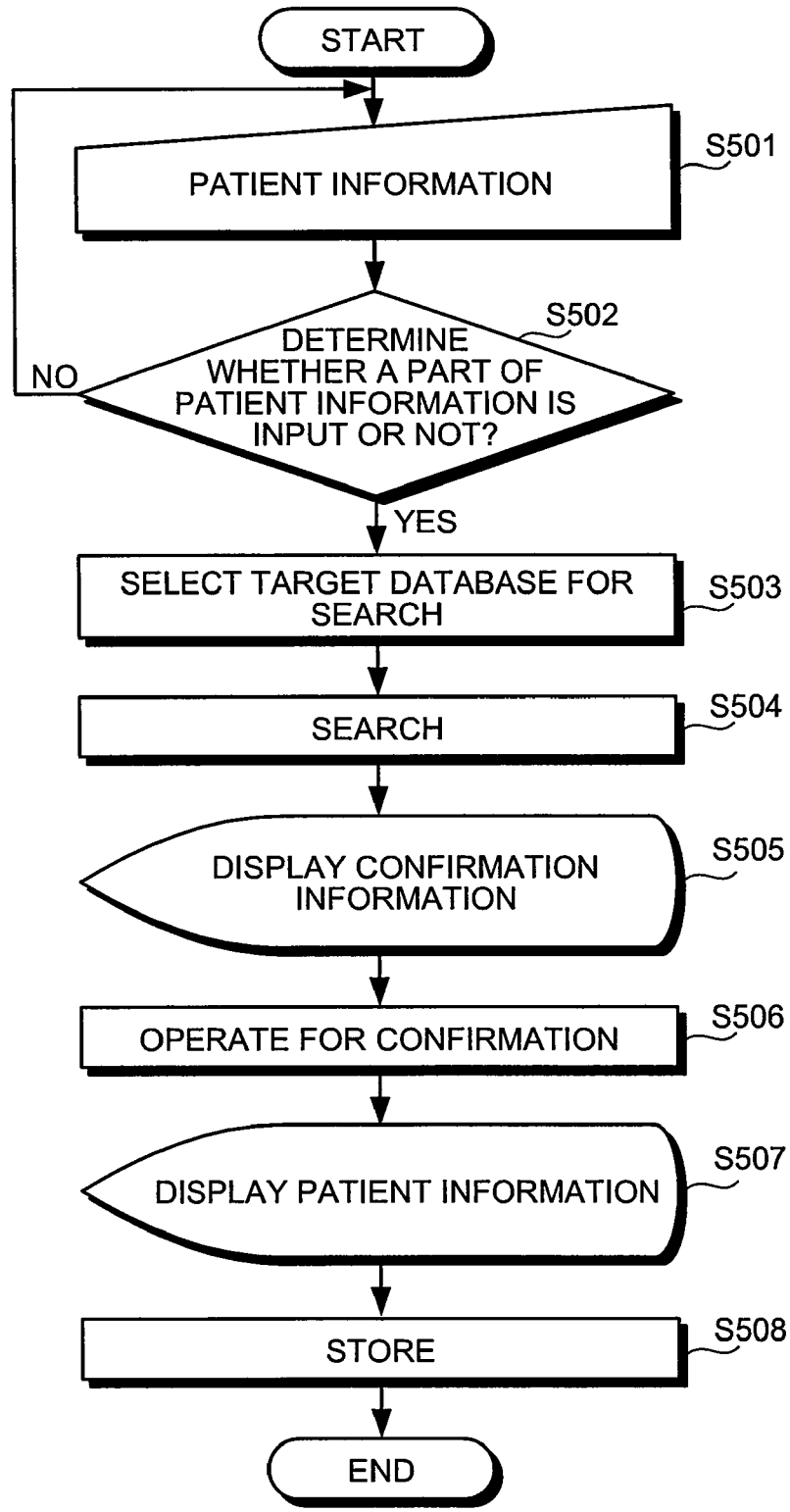
FIG. 16 is a flowchart for explaining a search operation of patient information performed by the filing system according to the fourth embodiment.
Figure 17:
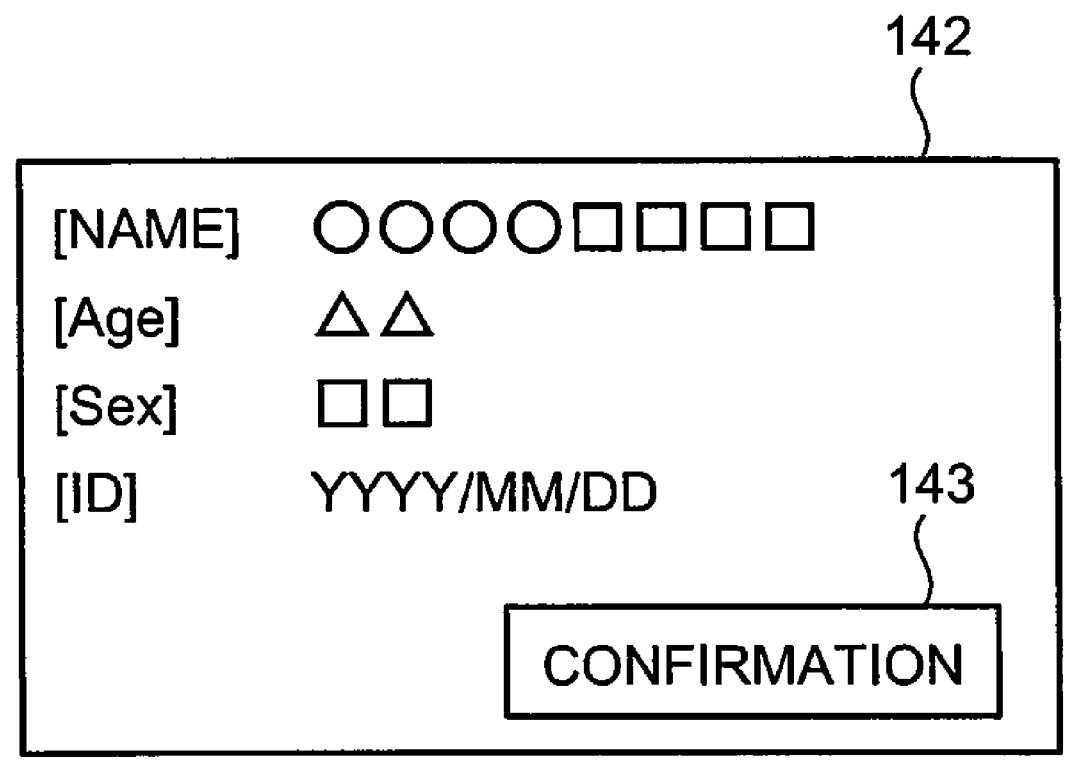

FIG. 15 is a schematic diagram of a configuration of a filing system including an image display apparatus according to a fourth embodiment; FIG. 16 is a flowchart for explaining a search operation of patient information in the filing system according to the fourth embodiment; and FIG. 17 is a diagram illustrating one example of the patient information to be displayed on the display unit 140 of the image display apparatus 104 according to the fourth embodiment. In FIG. 15, the fourth embodiment differs from the third embodiment in that a confirmation controller 153 is provided in the control unit 150 of the image display apparatus 104 as a confirmation controller for controlling the confirmation of the patient information. As shown in FIG. 17, the confirmation controller 153 displays, in the display area 142 of the display unit 140, name [NAME], age [Age], sex [Sex], and examination ID [ID] as the patient information which shows characteristics of the subject, and controls to display a confirmation button 143 which allows the user to confirm the patient information.

When the confirmation button 143 is right-clicked on by operating the mouse of the input unit 120 to move the cursor on the screen, confirmation completion information indicating that the patient information is confirmed is input to the confirmation controller 153. When the confirmation completion information is input, the confirmation controller 153 determines that the user has confirmed the patient information. The control unit 150 controls the interface 160 to transmit the patient information which is determined to have been confirmed by the user to the receiving device 102 via the communication cable 105.

Next, an operation for searching patient information in the filing system will be explained with reference to the flowchart in FIG. 16. In FIG. 16, when the user inputs one piece of patient information "Hanako Yamada" by operating the keyboard of the input unit 120 (step S501), at a time when input of at least a part of the information, e.g., "Yamada" is completed (Yes in step S502), the selector 152 selects the database 130 in the image display apparatus as a search target in the same way as in the third embodiment (step S503). On the other hand, when there is no input of such a search key (No in step S502), the process procedures return to step S501.

Next, in response to the selection of the database 130 by the selector 152, the search unit 151 searches the database 130 for patient information including the name of "Yamada", which is searched right before the current search, based on the history information (step S504). When the relevant patient information is found (Yes in step S505), the search unit 151 displays the searched patient information and the confirmation button 143 (see FIG. 17) in the display area of the display unit 140 (step S506).

When the mouse of the input unit 120 is operated to move the cursor on the screen, and a confirmation operation of right-clicking on the confirmation button 143 is performed (step S507), only the patient information is displayed on the screen (step S508).

Here, when the search unit 151 cannot find relevant patient information (No in step S505), the selector 152 selects the database 131 as a search target at step S503. In other words, the selector 152 repeats the selection process of the database as the search target until the search unit 151 finds patient information corresponding to the search key. This selection-information of the database in the selector 152 is transmitted to the server 106 via the interface 160. Then, the search unit 171 of the server 106 searches the database selected according to the selection-information, i.e., the database 131 selected by the selector 152, for patient information including the name of "Yamada", which is searched right before the current search, based on the history information (step S504). When the relevant patient information is found in the database 131 (Yes in step S505), the control unit 170 transmits the search result of patient information to the image display apparatus 104 via the interface 161.

When the search unit 151 of the image display apparatus 104 retrieves the patient information to finish the search process of the patient information, the control unit 150 displays confirmation information of the searched patient information and the confirmation button 143 in the display area of the display unit 140 (step S506). When the mouse of the input unit 120 is operated to move the cursor on the screen, and a confirmation operation of right-clicking on the confirmation button 143 is performed (step S507), only the patient information is displayed on the screen (step S508), and the patient information is stored in the database 130 (step S509). In the fourth embodiment, when there is no relevant patient name "Hanako Yamada", all pieces of patient information such as the patient name, age, sex, examination ID, and the like are input and stored in the database 130 (step S509).

The patient information whose content is confirmed is transmitted to the external device 102b of the receiving device 102 through the interface 160 under the control of the control unit 150. As a result, the external device 102b registers only the patient information whose content is confirmed by the user in the internal storage medium.

Next, a search operation performed in the image display apparatus 104 according to the fourth embodiment to search the case data of the subject will be explained. In the fourth embodiment, the control unit 150 follows substantially the same process procedures as the search process procedures of the patient information from step S501 to S509 mentioned above, so as to select the database as a search target of the case data, search the selected database for the case data of the subject based on a search key, i.e., at least a part of the patient information, perform a confirmation operation of the patient information of the case data corresponding to the search key, and display the searched case data on the display unit 140.

Specifically, when a search key, i.e., at least a part of the patient information (such as "Yamada" in the subject name "Hanako Yamada") is input by the input unit 120, the selector 152 selects the database as a search target for the case data in step S503, and repeats the selection process of the database until the search unit 151 finds the case data corresponding to the search key. The selector 152 first selects the database 130 in the image display apparatus 104 where information hit rate is high in the search process of case data. When the case data is not found in the database 130, the selector 152 selects the database 131 in the server 106.

On the other hand, in step S504 mentioned above, the search unit 151 searches the database (more specifically, the database 130 or 131) selected by the selector 152 for case data including a search key (e.g., a part of patient name in the patient information, such as "Yamada") input by the input unit 120 as a part of data. When the case data corresponding to the search key is stored in the database 130 of the apparatus (i.e., image display apparatus 104), the search unit 151 searches the database 130 for the relevant case data to finish the search process of the case data. On the other hand, when the case data corresponding to the search key is stored in the database 131 in the server 106, the search unit 171 of the server 106 searches the database 131 which is selected according to the selection-information from the selector 152 for the case data corresponding to the search key. The search unit 151 acquires the case data found through the search by the search unit 171 of the server 106 via the interface 160 to finish the search process of the case data. When plural pieces of case data including the search key are stored in each of the databases 130 and 131, the search units 151 and 171 search plural relevant pieces of case data.

In step S506 mentioned above, the confirmation controller 153 displays confirmation information of the patient information included in the case data searched by the search unit 151 together with the confirmation button 143 on the display unit 140. The confirmation controller 153 receives confirmation completion information from the input unit 120 when the confirmation button 143 is pressed in step S507. Based on the received confirmation completion information, the confirmation controller 153 determines that the patient information of the case data is confirmed by the user. When the search unit 151 finds plural pieces of case data as a result of search, the confirmation controller 153 displays confirmation information of each piece of patient information included in plural pieces of case data together with the confirmation button 143 on the display unit 140. The confirmation controller 153 receives instruction information instructing to select desired patient information from plural pieces of patient information and conformation completion information input by the input unit 120. The confirmation controller 153 determines that the desired patient information is confirmed, based on the instruction information and the confirmation completion information.

The control unit 150 displays case data of which patient information is determined to have been confirmed by the confirmation controller 153 on the display unit 140 in step S508. In this case, the control unit 150 displays intra-subject images, patient information, and the like included in the case data on the display unit 140 as shown in FIG. 3, for example.

Further, when at least one of the thumbnail and diagnosis data concerning the case data is generated, the control unit 150 updates the case data in the database 130 with the case data including newly-generated thumbnail data, diagnosis data, and the like in step S509 mentioned above. The control unit 150 can display the series of intra-subject images, patient information, thumbnail, diagnosis data, and the like included in the case data searched from the database 130 on the display unit 140. When the case data displayed on the display unit 140 is case data searched from the database 131 of the server 106, the control unit 150 stores the case data acquired from the server 106 in the database 130.

Thus in the fourth embodiment, the selector selects a database as a search target from plural databases similarly to the third embodiment, patient information of a target subject is searched from the data group in the selected database, and the searched patient information is confirmed. Therefore, it is possible to prevent a mistake in handling patient information and to improve the reliability of the searched patient information with the same advantages as in the third embodiment.

Thus in the fourth embodiment, the selector selects a database as a search target from plural databases similarly to the third embodiment, case data of a target subject is searched from the data group in the selected database, and the patient information included in the searched case data is confirmed. Therefore, it is possible to prevent a mistake in handling the patient information of the case data output and displayed at the examination or the diagnosis of the subject, and to improve the reliability of the searched case data with the same advantages as in the third embodiment.

In the second to fourth embodiments, the image display apparatus 104 having the function especially as a filing device is explained. However, the image display apparatus 104 may be combined with the function of the image display in the image display apparatus 4 according to the first embodiment. In the first embodiment, the image display apparatus 4 having the function especially of displaying images is explained. However, the image display apparatus 4 may be combined with the function as a filing device in the image display apparatus 104 according to the second to fourth embodiments. For example, the control unit 15 of the image display apparatus 4 according to the first embodiment may include the search unit 151, the selector 152, and the confirmation controller 153 as appropriate. The control unit 150 of the image display apparatus according to the second to the fourth embodiments may include the image display controller 15a and the image processing controller 15b mentioned earlier.

Further, in the second to the fourth embodiment described above, at least a part of information included in the patient information is input as a search key of the patient information or the case data. The search key is not limited thereto. For example, at least a part of information included in the case data, such as at least a part of identification information identifying a subject, such as patient information or diagnosis data of a subject may be input as a search key, and patient information or case data corresponding to the search key may be searched.

The image display apparatus according to the present invention can quickly search patient information of a desired subject from patient information of plural subjects stored in the database, quickly transmits the searched patient information of the subject to the receiving device of intra-subject images, and reduce labor required for an input of patient information at a time of registration of the patient information to the receiving device.

The image display apparatus according to the present invention is useful as an image display apparatus which displays a series of images captured inside the subject, such as a patient, more specifically as an image display apparatus which can search patient information of a desired subject from a database storing patient information of plural subjects, and easily transmit the searched patient information to a receiving device of a group of intra-subject images.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image display apparatus comprising:
a database that stores patient information including plural pieces of information of a subject; a display unit that displays a group of intra-subject images of the subject captured by a capsule endoscope and patient information; an input unit that inputs at least a part of information included in patient information of a desired subject;
a control unit that searches the patient information of plural subjects stored in the database for the patient information of the desired subject based on the at least a part of information input by the input unit, to display the searched patient information on the display unit; and
a communication unit that transmits the patient information searched by the control unit to an external receiving device that receives a group of intra-subject images from the capsule endoscope in the desired subject;
wherein the input unit inputs confirmation completion information indicating that the patient information searched by the control unit is confirmed, and
the control unit determines that confirmation of the patient information is completed based on the confirmation completion information, and controls the communication unit to transmit the patient information whose confirmation is completed to the external receiving device.

2. The image display apparatus according to claim 1, wherein the database stores case data which includes at least patient information of a subject and a group of intra-subject images, the input unit inputs at least a part of information in related information of the desired subject, and the control unit searches case data of plural subjects stored in the database for case data including the at least a part of information input by the input unit to display the searched case data on the display unit.

3. The image display apparatus according to claim 2, wherein the related information is one of patient information and diagnosis data of a subject.

4. The image display apparatus according to claim 1, wherein the control unit searches for plural pieces of patient information including the at least a part of information input by the input unit, to display a list of searched plural pieces of patient information on the display unit.

5. The image display apparatus according to claim 2, wherein the control unit searches for plural pieces of case data including the at least a part of information input by the input unit, to display a list of searched plural pieces of case data on the display unit.

6. The image display apparatus according to claim 1, wherein the communication unit is selectively connected to one of an external server having a database storing patient information of plural subjects and an external receiving device for communication, and the control unit selects one of the database of the external server connected to the communication unit for communication and the database, searches the patient information of plural subjects stored in the database selected for patient information including the at least a part of information input by the input unit, and displays the searched patient information on the display unit.

7. The image display apparatus according to claim 2, wherein the communication unit is selectively connected to one of an external server having a database storing case data of plural subjects and an external receiving device for communication, the control unit selects one of the database of the external server connected to the communication unit for communication and the database, searches the case data of plural subjects stored in the database selected for case data including the at least a part of information input by the input unit, to display the searched case data on the display unit.

8. The image display apparatus according to claim 2, wherein the control unit determines that confirmation of the patient information is completed based on the confirmation completion information, and displays the case data including the patient information whose confirmation is completed on the display unit.

* * * * *